United States Patent
Behr et al.

(10) Patent No.: US 9,676,798 B2
(45) Date of Patent: Jun. 13, 2017

(54) CATIONIC OLIGONUCLEOTIDES, AUTOMATED METHODS FOR PREPARING SAME AND THEIR USES

(71) Applicants: CENTRE NATIONAL DE LA RECHERCHE SCIENTIFIQUE (CNRS), Paris (FR); UNIVERSITE DE STRASBOURG, Strasbourg (FR); POLYPLUS TRANSFECTION, Illkirch (FR)

(72) Inventors: Jean-Paul Behr, Strasbourg (FR); Mitsuharu Kotera, Strasbourg (FR); Benedicte Pons, Grenoble (FR); Emilie Voirin, Lipshein (FR); Jean-Serge Remy, Neugartheim (FR)

(73) Assignees: CENTRE NATIONAL DE LA RECHERCHE SCIENTIFIQUE (CNRS), Paris (FR); UNIVERSITE DE STRASBOURG, Strasbourg (FR); POLYPLUS TRANSFECTION, Illkirch (FR)

( * ) Notice: Subject to any disclaimer, the term of this patent is extended or adjusted under 35 U.S.C. 154(b) by 0 days.

(21) Appl. No.: 14/745,871

(22) Filed: Jun. 22, 2015

(65) Prior Publication Data
US 2016/0280728 A1  Sep. 29, 2016

Related U.S. Application Data

(62) Division of application No. 12/086,599, filed as application No. PCT/IB2006/004085 on Dec. 14, 2006, now Pat. No. 9,090,648.

(60) Provisional application No. 60/750,346, filed on Dec. 15, 2005.

(51) Int. Cl.
| C07H 21/00 | (2006.01) |
| C07F 9/22 | (2006.01) |
| A61K 47/48 | (2006.01) |
| A61K 48/00 | (2006.01) |
| C12N 15/88 | (2006.01) |

(52) U.S. Cl.
CPC .......... *C07F 9/22* (2013.01); *A61K 47/48192* (2013.01); *C07H 21/00* (2013.01); *A61K 48/0041* (2013.01); *C12N 15/88* (2013.01)

(58) Field of Classification Search
None
See application file for complete search history.

(56) References Cited

U.S. PATENT DOCUMENTS

| 6,071,890 A | 6/2000 | Scheule et al. |
| 7,772,201 B2 | 8/2010 | Mixson |
| 8,399,422 B2 | 3/2013 | Neuberg et al. |

| 2003/0100113 A1 | 5/2003 | Behr et al. |
| 2004/0019008 A1 | 1/2004 | Lewis et al. |
| 2004/0204377 A1 | 10/2004 | Rana |
| 2006/0002991 A1 | 1/2006 | Essler et al. |

(Continued)

FOREIGN PATENT DOCUMENTS

| JP | 2004-137143 | 5/2004 |
| WO | WO 2004/110499 | 12/2004 |

(Continued)

OTHER PUBLICATIONS

Langenegger et al. Helvetica Chimica Acta (2002), vol. 85, pp. 3414-3421.*
de la Torre et al, "Synthesis and Binding Properties of Oligonucleotides Carrying Nuclear Localization Sequences", Bioconjugate Chemistry, 1999, v. 10:1005-12.
Chiu et al, "Visualizing a correlation between siRNA localization, cellular uptake, and RNAi in living cells", 2004, Chemistry & Biology, vol. 11, pp. 1165-1175.
Lodish et al, "General Structure of Proteins, Hydrophilic Amino Acids", Molecular Cell Biology, Third edition, New York, Scientific American Books, 1995, p. 55.
Ilies et al, "Pyridinium cationic lipids in gene delivery: as in vitro and in vivo comparison of transfection efficiency versus a tetraalkylammonium congener", Archives of Biochemistry and Biophysics 435 (2005); 217-226.

(Continued)

*Primary Examiner* — Patrick Lewis
(74) *Attorney, Agent, or Firm* — Nixon & Vanderhye P.C.

(57) ABSTRACT

The invention relates to oligonucleotide-oligocation molecules $A_iB_jH$ that can be synthetized via automated phosphoramidite chemistry having oligonucleotides moieties Ai and oligocations moieties Bj, wherein $A_i$ is an i-mer oligonucleotide residue, with i=5 to 50, where nucleotide A is an oligomer with naturally or non naturally occurring nucleobases and/or pentafuranosyl groups and/or native phosphodiester bonds, for example selected from the group comprising deoxyribo, ribo, locked (LNA) nucleotides as well as their chemical modifications or substitutions such as phosphorothioate, 2'-fluoro, 2'-O-alkyl, or a marker group such as a fluorescent agent, $B_j$ is a j-mer organic oligocation moiety, with j=1 to 50, where B is selected from the group comprising .—$HPO_3$—$R^1$—$(X$—$R^2{}_n)_{n1}$—$X$—$R^3$—$O$—, where $R^1$, $R^2$n and $R^3$, identical or different, are lower alkylene, X is NH or $NC(NH_2)_2$, n varies from 1 to 5 and n1=2 to 20, .—$HPO_3$—$R^4$—$CH(R^5X^1)$—$R^6$—$O$—, where $R^4$ is lower alkylene, $R^5$ and $R^6$, identical or different, are lower alkylene and $X^1$ is putrescine, spermidine or spermine residue, .—$HPO_3$—$R^7$-$(aa)_{n2}$-$R^8$—$O$—, where $R^7$ is lower alkylene and $R^8$ is lower alkylene, serine, a natural aminoalcohol, $(aa)_{n2}$ is a peptide containing natural aminoacids with cationic side chains, such as Arginine, Lysine, Ornithine, -Histidine, Diaminopropionic acid and n2=2 to 20.

5 Claims, 22 Drawing Sheets

(56) References Cited

U.S. PATENT DOCUMENTS

| | | |
|---|---|---|
| 2006/0019912 A1 | 1/2006 | Burkoth et al. |
| 2009/0069262 A1 | 3/2009 | Behr |
| 2009/0074852 A1 | 3/2009 | Kaufmann et al. |
| 2011/0118331 A1 | 5/2011 | Behr et al. |

FOREIGN PATENT DOCUMENTS

| | | |
|---|---|---|
| WO | 2006/052854 | 5/2006 |
| WO | 2007/069092 | 6/2007 |

OTHER PUBLICATIONS

Quek et al, "Synthesis and properties of N,N'-dialkylimidazolium bis(nonafluorobutane-1-sulfonyl)imides: a new subfamily of ionic liquids", Tetrahedron 62 (2006) 3137-3145.

Chen Jian-hai et al "Application of cationic polymer vector for gene delivery systems" Acta Pharmaceutica Sinica, vol. 38, No. 4, pp. 316-320 (Apr. 30, 2003).

Schmid et al, "Recognition of DNA Sequences by Strand Replacement with Polyamino-oligonucleotides", Tetrahedron Letters, vol. 36, No. 9, pp. 1447-1450, 1995.

Dias et al, "Antisense Oligonucleotides; Basic Concepts and Mechanisms", Molecular Cancer Therapeutics, Mar. 2002 1; 347 (11 pages).

International Search Report for PCT/IB2009/050379, mailed Jun. 17, 2009.

Moschos et al., "Lung Delivery Studies using SIRNA Conjugated to TAT (48-60) and Penetratin Reveal Peptide Induced Reduction in Gene Expression and Induction of Innate Immunity", Bioconjugate Chemistry Sep.-Oct. 2007 vol. 18, No. 5, pp. 1450-1459.

Muratovska et al., "Conjugate for Efficient Delivery of Short Interfering RNA (SIRNA) into Mammalian Cells", FEBS Letters Jan. 30, 2004, vol. 558, No. 1-3, pp. 63-68.

Pons, Bénédicte et al., "Online Synthesis of Diblock Cationic Oligonucleotides for Enhanced Hybridization to Their Complementary Sequence", Chembiochem, vol. 7, No. 8, pp. 1173-1176, (2006).

Chen, Chang-Po et al., "A Concise Method for the Preparation of Peptide and Arginine-Rich Peptide-Conjugated Antisense Oligonucleotide", Bioconjugate Chemistry, vol. 14, No. 3, pp. 532-538, (May 2003).

Pitié, Marguerite et al., "Cleavage of Double-Stranded DNA by Manganese Tris (Methylpyridiniumyl) Porphyrin Linked to 3'-Spermine Oligonucleotides" JBIC. Journal of Biological Inorganic Chemistry, vol. 1, No. 3, pp. 239-246, (Feb. 1996).

Sund, Christian et al., "Synthesis of C-Branched Spermine Tethered Oligo-DNA and the Thermal Stability of the Duplexes and Triplexes", Tetrahedron, vol. 52, No. 37 pp. 12275-12290, (1996).

Ching-Hsuan, Tung et al., "Polyamine-Linked Oligonucleotides for DNA Triple Helix Formation", Nucleic Acids Research, vol. 21, No. 23, pp. 5489-5494, (1993).

International Search Report for PCT/IB2006/004085, mailed Feb. 11, 2008.

Written Opinion of the International Searching Authority for PCT/IB2006/004085, mailed Feb. 11, 2008.

\* cited by examiner

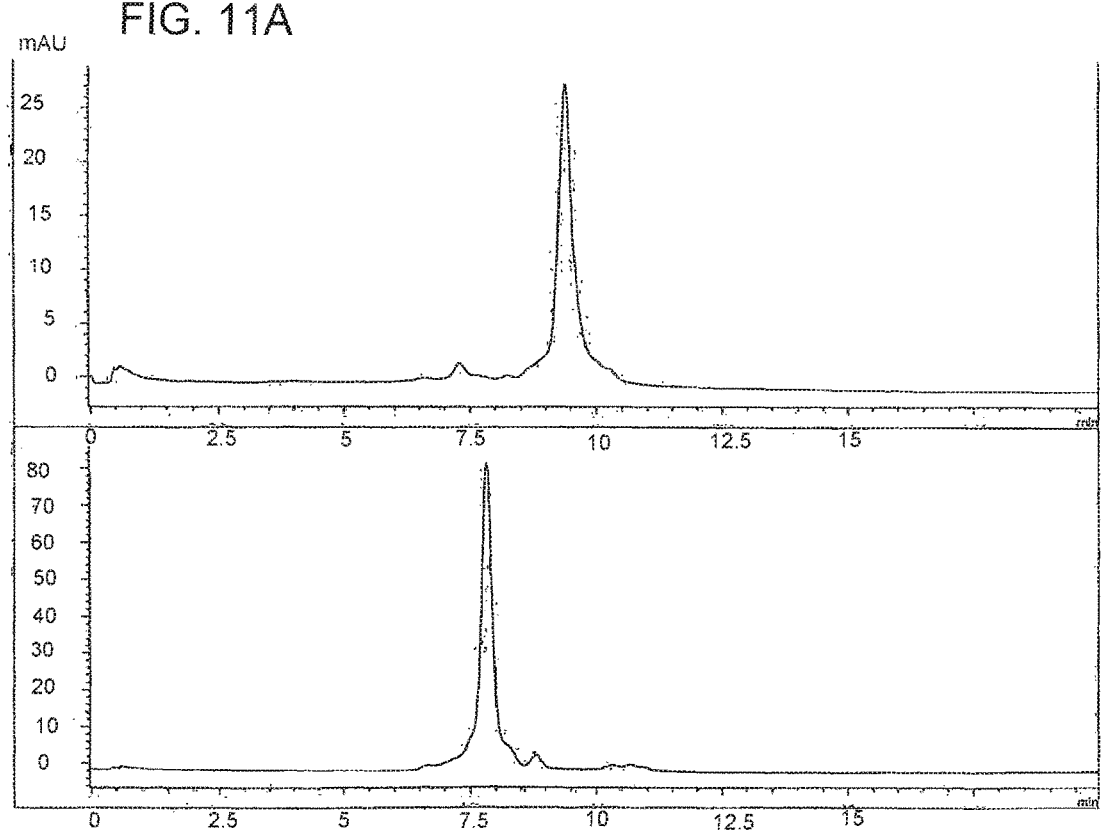

FIG. 13A
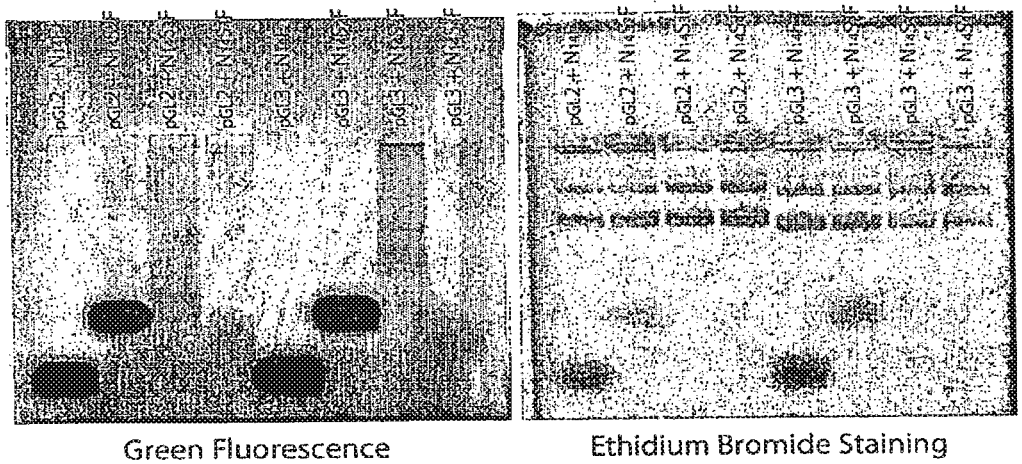
Green Fluorescence        Ethidium Bromide Staining
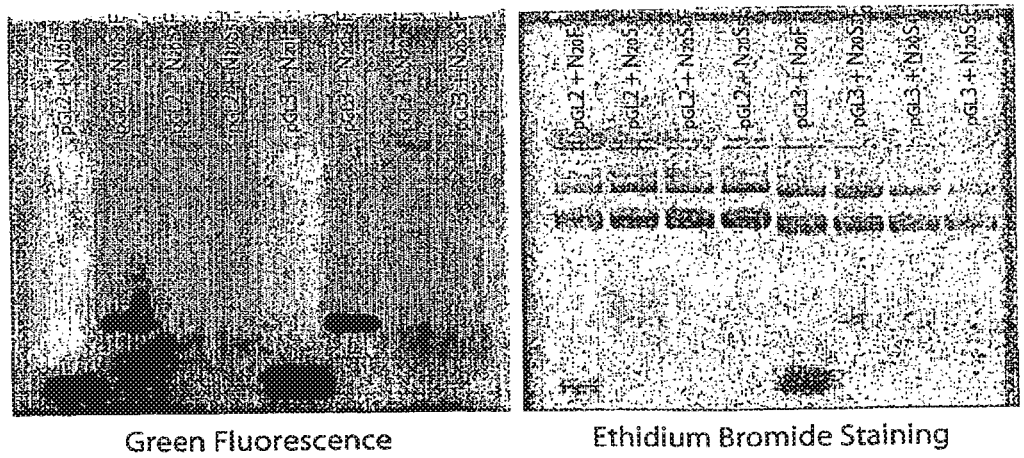
Green Fluorescence        Ethidium Bromide Staining
FIG. 13B

CATIONIC OLIGONUCLEOTIDES, AUTOMATED METHODS FOR PREPARING SAME AND THEIR USES

This application is a divisional of U.S. application Ser. No. 12/086,599 (published as US 2009-0069262 A1), filed Jun. 16, 2008 (issued as U.S. Pat. No. 9,090,648B2 on Jul. 28, 2015), which is a U.S. national phase of International Application No. PCT/IB2006/004085, filed 14 Dec. 2006, which designated the U.S. and claims the benefit of U.S. Provisional Application No. 60/750,346, filed 15 Dec. 2005, the entire contents of each of which are hereby incorporated by reference.

The invention relates to cationic oligonucleotides, i.e, oligonucleotide-oligocation molecules, also called cationic oligonucleotides in the description (irrespective of their global charge) that can be synthetized stepwise on an oligonucleotide synthesizer. It also pertains to their use, in molecular biology, diagnostics and therapeutic applications.

Oligonucleotides find an extremely large number of applications in molecular biology and diagnostics, and may become a very selective class of drugs for the treatment of a vast palette of diseases.

Oligonucleotides are polyanions that exert their specific activity following hybridization to a complementary sequence borne by another polyanionic nucleic acid, As drug candidates, they must also be capable of crossing the anionic cell membrane.

Simple electrostatic considerations imply that hybridization energy and cell binding could benefit from the addition of cationic groups to the oligonucleotide structure.

Towards this goal, many synthetic approaches for introducing ammonium or guanidinium residues into oligonucleotides have been explored: phosphate backbone replacement, ribose or nucleic base modification, and end conjugation of a polycation. However, hybridization specificity, nucleic acid-processing enzyme activity as well as metabolite toxicity concerns all point to the block approach, where the polycation is appended to an otherwise natural oligonucleotide, as the best solution. Unfortunately, stepwise automated synthesis of oligonucleotide-cationic peptide conjugates is not yet routine. On the other hand, conjugation chemistry between preformed large blocks is not straightforward, especially in water, where <<super>> zwitterions raise intractable solubility, purification and characterization problems. Moreover, molecular biology and diagnostics applications require fast and straightforward synthesis of any given base sequence linked to any organic cation length.

The inventors have found that an online, computer driven, synthesis of oligonucleotide-oligocation molecules was possible by plugging vials containing properly activated and protected oligocationic derivatives to an oligonucleotide synthesizer in addition to those of the four natural bases.

An object of the invention is thus to provide new cationic oligonucleotides.

Another object of the invention is to provide a high yield, automated synthesis of said cationic oligonucleotides.

In a further object, the invention relates to the applications of said cationic oligonucleotides, particularly in molecular biology, diagnostics and therapeutics.

The invention thus relates to mixed oligonucleotide oligocation molecules that can be synthetized via automated phosphoramidite chemistry, i.e., polyphosphodiesters.

More particularly, the cationic oligonucleotides $A_iB_jH$ of the invention have oligonucleotides moieties Ai and oligocations moieties Bj, wherein $A_i$ is an i-mer oligonucleotide residue, with i=5 to 50 with naturally or non naturally occurring nucleobases and/or pentafuranosyl groups and/or native phosphodiester bonds, .Bj is a j-mer organic oligocation moiety, with j=1 to 50, where B is selected from the group comprising —H—$PO_3R^1$—(X—$R^2$)$_{n1}$—X—$R^3$—O—, wherein $R^1$, $R^2$ and $R^3$, identical or different, are lower alkylene, X is NH or $NC(NH_2)_2$, and n1=2 to 20, —$HPO_3$-$R^4$—CH($R^5X^1$)—$R^6$-0-, where $R^4$ is lower alkylene, $R^5$ and $R^6$, identical or different, are lower alkylene and $X^1$ is putrescine, spermidine or spermine residue, —H—$PO_3$—$R^7$-(aa)$_{n2}$-$R^8$-0-, where $R^7$ is lower alkylene and $R^8$ is lower alkylene, serine, an aminoalcohol, (aa)$_{n2}$ is a peptide containing natural aminoacids with cationic side chains, such as Arginine, Lysine, Ornithine, Histidine, Diaminopropionic acid and n2=2 to 20.

"Lower alkyl" and "lower alkylene", as used in the description and the claims, preferably designate an optionally substituted C1-C5 linear or branched alkyl or alkylene radical, respectively.

A is for example selected from the group comprising deoxyribo, ribo, locked (LNA) nucleotides as well as their chemical modifications or substitutions such as phosphorothioate (also designated thiophosphate), 2'-fluoro, 2'-O-alkyl or a marker group such as a fluorescent agent.

Mixed oligonucleotide-oligocation molecules of the invention have $^{3'}A^{5'}$-B sequence.

Other molecules of the invention have B-$^{3'}A^{5'}$ sequence.

Still other molecules of the invention have B-$^{3'}A^{5'}$-B or $^{3'}A^{5'}$-B-$^{3'}A^{5'}$ sequence.

Such a sequence is illustrated in the examples by an oligonucleotide-spermine molecule having the following structure:

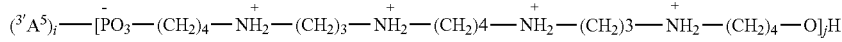

$(^{3'}A^5)_i$—[$PO_3$—$(CH_2)_4$—$\overset{+}{NH_2}$—$(CH_2)_3$—$\overset{+}{NH_2}$—$(CH_2)4$—$\overset{+}{NH_2}$—$(CH_2)3$—$\overset{+}{NH_2}$—$(CH_2)_4$—O]$_j$H wherein A, i and j are as above defined.

Molecules with A being a phosphorothioate nucleotide are particularly advantageous in view of their biological applications, since phosphorothioate oligonucleotides are not hydrolyzed in biological fluids.

The above defined cationic oligonucleotides form fast and stable complexes with their complementary sequence in a strand replacement context and even in a plasmid strand invasion context, as illustrated by the examples.

Due to end conjugation, sequence selectivity remains as high as for natural nucleotides.

Accordingly, the cationic oligonucleotides of the invention are of great interest for molecular biology, research reagents and diagnostics applications, such as PCR, real-time PCR, genotyping, in situ hybridization and DNA chips.

Such applications are then also covered by the invention and comprise the use of oligonucleotide-oligocation molecules such as above defined.

In contrast to anionic oligonucleotides, cationic oligonucleotides of the invention are shown in the examples to spontaneously enter the cytoplasm and nucleus of living cells.

In view of their enhanced hybridization and cell permeation properties, they are also useful for therapeutic approaches, such as those mediated by antisense and siRNA degradation of messenger RNA, by exon skipping during messenger RNA maturation, by triple helix formation with chromatin, by chromatin strand invasion (gene correction).

The invention thus also relates to pharmaceutical compositions comprising an effective amount of oligonucleotide-oligocation molecules such as above defined, in association with a pharmaceutically acceptable carrier.

The invention also relates to a method of treatment comprising using an effective amount of oligonucleotide-oligocation molecules such as above defined, in association with a pharmaceutically acceptable carrier.

The above defined mixed oligonucleotide-oligocation molecules are advantageously stepwise synthetized on an oligonucleotide synthesizer, via the phosphoramidite route, according to a method comprising plugging vials containing activated and protected oligocations B to an oligonucleotide synthesizer, in addition to vials of oligonucleotides A such as above defined, or the reverse, stopping the synthesis, when the desired length is obtained, cleaving the oligomers from the solid support, and removing the protecting groups.

The invention is closely related to the phosphoramidite reagents used in the automated synthesis for the construction of oligocation repeated block B. The 20 following phosphoramidite reagents can be used for this purpose:

$P(OR^9)(N(R^{10})_2)$—O—$R^1$—(X—$R^2$)—X—$R^3$—O-Prot where $R^1$, $R^2$, $R^3$, and n1 are as above defined, X is suitably protected NH or $NC(NH_2)_2$, $R^9$ is —$CH_2CH_2CN$, or lower alkyl, $R^{10}$ is lower alkyl, or —$N(R^{10})_2$ is pyrrolidino, piperidino or morpholino group, and Prot is a protecting group used in oligonucleotide synthesis, such as DMT, MMT;

$P(OR^9)(N(R^{10})_2)$—O—$R^4$—CH($R^5$X1)—$R^6$—O-Prot, where $R^4$, $R^6$, $R^6$ are lower alkylene, $X^1$ is suitably protected putrescine, spermidine or spermine, $R^9$ and $R^{10}$ are as above defined;

$P(OR^9)(N(R^{10})_2)$—O—$R^7$-(aa)$_{n2}$-$R^8$—O-Prot, where $R^7$, $R^8$, $R^9$, $R^{10}$, n2, and Prot are as above defined, (aa)$_{n2}$ is a peptide containing natural aminoacids with suitably protected cationic side chains, such as Arginine, Lysine, Ornithine, Histidine, Diaminopropionic acid and n2=2 to 20.

Suitably protected NH or $NC(NH_2)_2$ means that protecting groups are present on the amino or guanidine residue, respectively, to render their functionality inert to chemical reaction conditions to which the reagent is exposed.

Such protecting groups are for example phthalimide (PHTH), trifluoroacetate, allyloxycarbonyl (Alloc), benzyloxycarbonyl (CBZ), chlorobenzyloxycarbonyl, t-butyloxycarbonyl (Boc), fluorenylmethoxycarbonyl (Fmoc) and isonicotinyloxy (i-Noc) groups.

According to an embodiment of the invention, stepwise synthesis of the oligonucleotide sequence is followed by stepwise synthesis of the oligocation moiety to obtain compounds having sequence ($^{3'}A^{5'}$-B).

According to another embodiment, reverse steps are performed, the stepwise synthesis of oligocation moiety being followed by stepwise synthesis of the oligonucleotide sequence to obtain compounds of (B-$^{3'}A^{5'}$) sequence.

According to still another embodiment, mixed sequences are synthetized.

In particular, oligonucleotide sequences capped at both ends (B-$^{3'}A^{5'}$-B) can resist exonucleases in biological fluids, and cation-interrupted sequences ($^{3'}A^{5'}$-B-$^{3'}A^{5'}$) allow targeting of vicinal nucleic acid sequences.

By using naturally occurring amines like spermine, or peptides such as oligoarginines, potential toxicity of metabolites is avoided. Spermine is indeed present at millimolar concentration in cells and its end-alkylation is harmless. Moreover, basic peptide sequences are present in many nuclear proteins.

The activated and protected oligocations B are advantageously obtained by protecting the amino groups of a polyamine, followed by α, ω-bis hydroxylalkylation, leading to diols compatible with oligonucleotide synthesis.

Classical DMT and phosphoramidite elongation chemistry is advantageously implemented together with base-labile TFA protecting groups.

The chemically protected diols are new products and enter into the scope of the invention.

The invention particularly relates to the intermediates selected from the group comprising $P(OR^9)(N(R^{10})_2)$—O—$R^1$—(X—$R^2$)—X—$R^3$—O-Prot where $R^1$, $R^2$, $R^3$, and n1 are as above defined, X is suitably protected NH or $NC(NH_2)_2$, $R^9$ is —$CH_2CH_2CN$, or lower alkyl, $R^{10}$ is lower alkyl, or —$N(R^{10})_2$ is pyrrolidino, piperidino or morpholino group, and Prot is a protecting group used in oligonucleotide synthesis, such as DMT, MMT; $P(OR^9)(N(R^{10})_2)$—O—$R^4$—CH($R^5$—X1)-$R^6$—O-Prot, where $R^4$, $R^5$, $R^6$ are lower alkylene, $X^1$ is suitably protected putrescine, spermidine or spermine, $R^9$ and $R^{10}$ are as above defined; $P(OR^9)(N(R^{10})_2)$—O—$R^7$-(aa)$_{n2}$-$R^8$—O-Prot, where $R^7$, $R^8$, $R^9$, $R^{10}$, n2, and Prot are as above defined, (aa)$_{n2}$ is a peptide containing natural aminoacids with suitably protected cationic side chains, such as Arginine, Lysine, Ornithine, Histidine, Diaminopropionic acid and n2=2 to 20.

Other characteristics and advantages of the invention are given hereinafter. In particular, the synthesis of decamer oligonucleotide sequences ($A_{10}$) with spermine (S), designated by $A_{10}S_n$ in the following will be given by way of illustration, without limiting the invention. In the examples, it will be referred to FIGS. 1 to 14, which represent, respectively:

BRIEF DESCRIPTION OF THE DRAWINGS

FIG. 7A deconvoluted—ESI-MS of N10S1; m/z calcd. 3419.84, found 3419.80—comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2), FIG. 7C deconvoluted—ESI-MS of N10S2; m/z calcd. 3828.12, found 3829.12—comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2), FIG. 7E deconvoluted—ESI-MS of N10S3; m/z calcd. 4236.44, found 4238.40—comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2)

FIG. 13B, strand invasion of pGL2 and pGL3 plasmids by $N_{20}S_nF$.

EXAMPLE 1: SYNTHESIS OF PHOSPHORAMIDITE SPERMINE SYNTHON

Figure 1A:
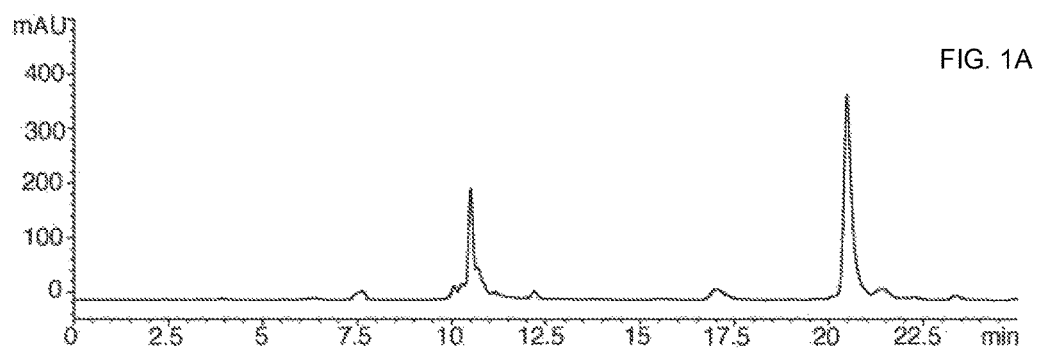
FIG. 1A is HPLC analysis of cationic oligonucleotides $N_{10}S_n$ (n=1-2) on a reverse phase column—HPLC of $N_{10}S_1$ crude DMT-ON, FIG. 1B is HPLC analysis of cationic oligonucleotides $N_{10}S_n$ (n=1-2) on a reverse phase column—HPLC of $N_{10}S1$ purified.
Figure 1B:
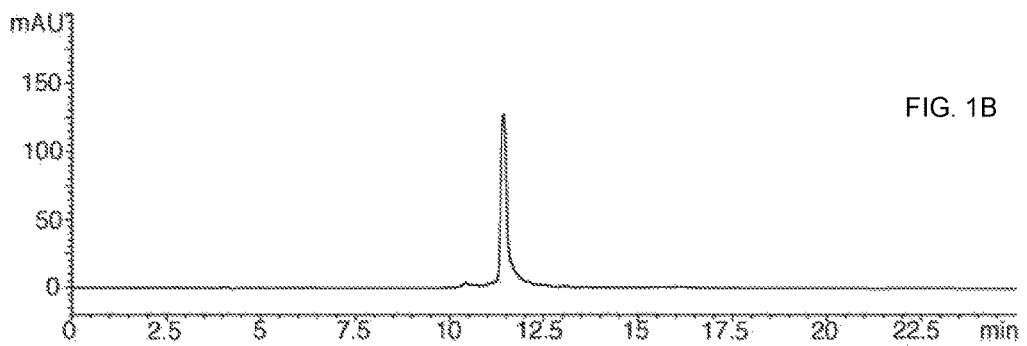
FIG. 1C is HPLC analysis of cationic oligonucleotides $N_{10}S_n$ (n=1-2) on a reverse phase column—HPLC of $N_{10}S_2$ crude, DMT-ON, FIG. 1D is HPLC analysis of cationic oligonucleotides $N_{10}S_n$ (n=1-2) on a reverse phase column—HPLC of $N_{10}S_2$ purified.
Figure 1C:
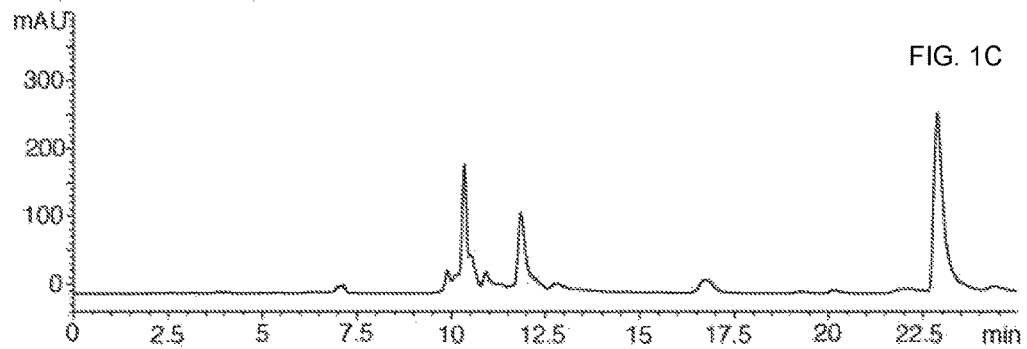
Figure 1D:
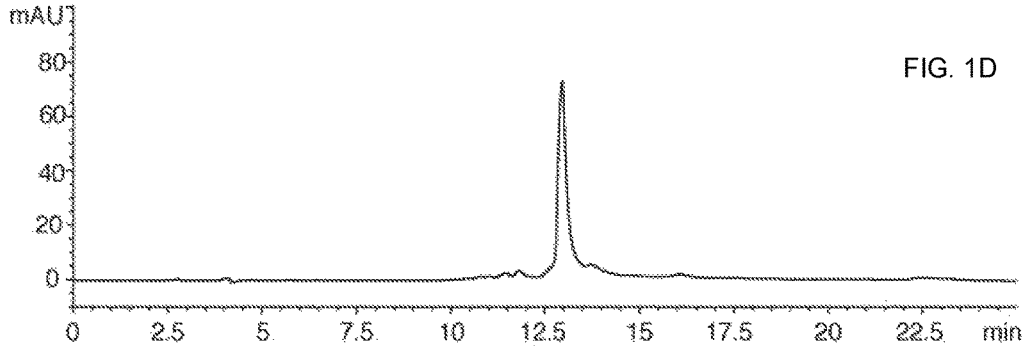
Figure 2A:
FIG. 2A is HPLC analysis of purified oligonucleotides $N_{10}S_n$ (n=1-6) on an anion exchange column—HPLC of $N_{10}S_1$.
Figure 2B:
FIG. 2B is HPLC analysis of purified oligonucleotides $N_{10}S_n$ (n=1-6) on an anion exchange column—HPLC of $N_{10}S_2$.
Figure 2C:
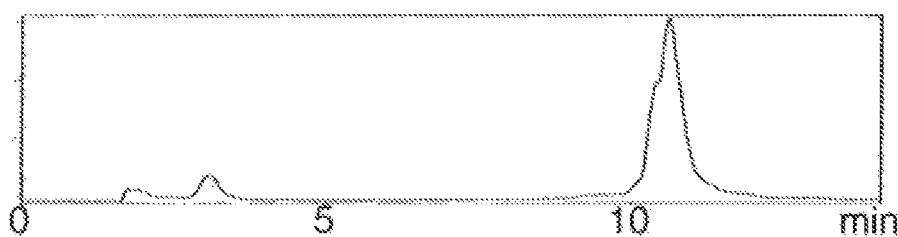
FIG. 2C is HPLC analysis of purified oligonucleotides $N_{10}S_n$ (n=1-6) on an anion exchange column—HPLC of $N_{10}S_3$.
Figure 2D:
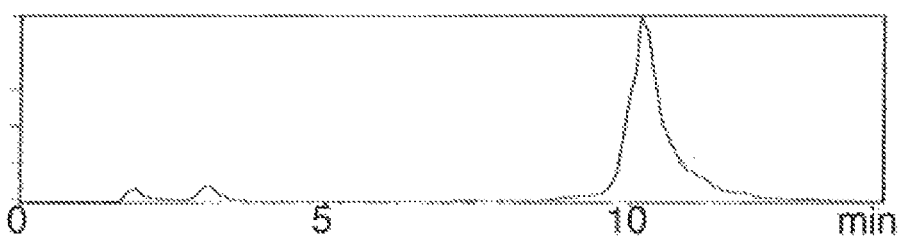
FIG. 2D is HPLC analysis of purified oligonucleotides $N_{10}S_n$ (n=1-6) on an anion exchange column—HPLC of $N_{10}S_4$.
Figure 2E:
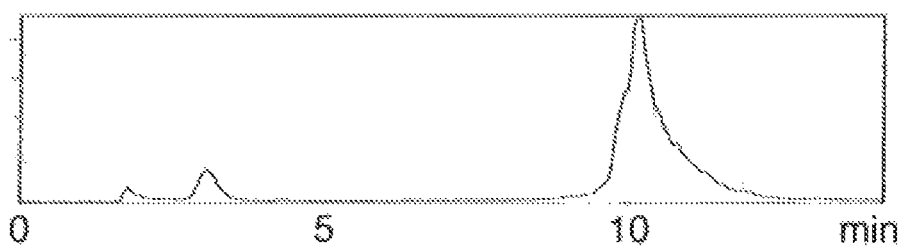
FIG. 2E is HPLC analysis of purified oligonucleotides $N_{10}S_n$ (n=1-6) on an anion exchange column—HPLC of $N_{10}S_5$.
Figure 2F:
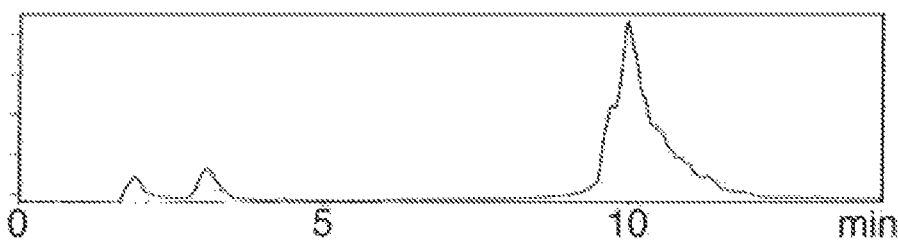
FIG. 2F is HPLC analysis of purified oligonucleotides $N_{10}S_n$ (n=1-6) on an anion exchange column—HPLC of $N_{10}S_6$, FIG. 3, analysis of $N_{10}S_n$ (n=1-6) electrophoretic mobility by polyacrylamide gel electrophoresis, FIG. 4, spontaneous exchange of $N_{10}$ with $N_{10}C_{10}$ at various temperatures, FIG. 5, strand exchange between $N_{10}$ and $N_{10}Sn$ as revealed by polyamide gel electrophoresis, FIG. 6, melting temperatures of $N_{10}S_nC_{10}$ duplexes (where C is the nucleotide complementary to N)

The spermine tethered phosphoramidite 1 was synthesized from spermine as shown in following Scheme 1:

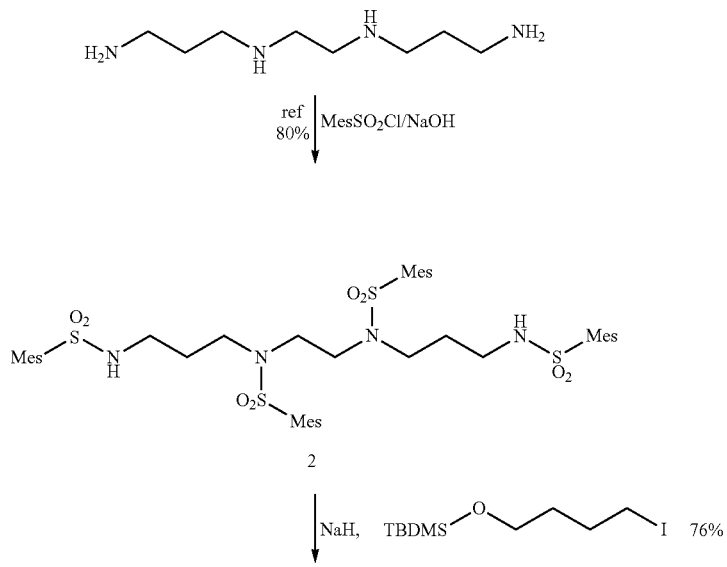

-continued

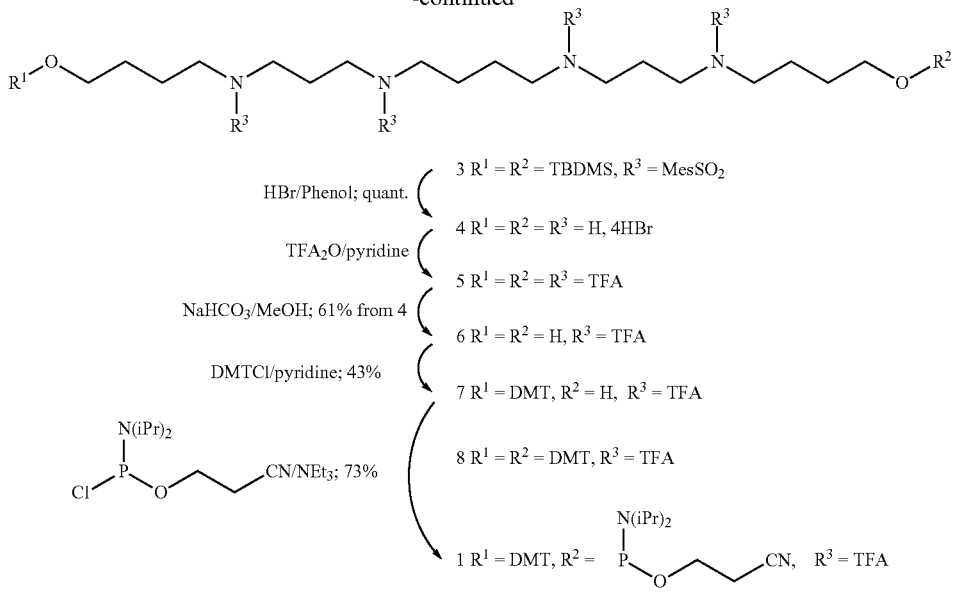

(Mes=2,4,6-trimethylphenyl; TBDMS=t-butyldimethylsilyl; TFA=$CF_3CO$—; DMT=4,4'-dimethoxytrityl)

Tetrakis(mesitylsufonyl)spermine 2, prepared from spermine, was bis-alkylated to 3. After complete deprotection of 3 in acidic conditions, the crude bis(C4-OH)spermine tetrahydrobromide 4 was fully protected by trifluoroacetic anhydride in pyridine, then the two terminal ester group of 5 were hydrolyzed in neutral conditions to diol 6. Mono tritylation of 5 was performed in statistical way using one molar equivalent of DMTCl reagent to afford 7 in 43% yield. Unreacted diol 6 and bis-trityl compound 8 were recovered and re-equilibrated in mild acidic conditions (trifluororoacetic acid in dichloromethane) to afford 7. Phosphitylation of 7 gave the desired phosphoramidite 1.

$N^1,N^4,N^9,N^{12}$-Tetrakis(mesitylsulfonyl)spermine (2): This compound was prepared according to the reference: Bergeron et al. J. Med. Chem. 2001, 44, 232-244.

$N^1,N^{12}$-Bis[4-(f-butyldimethylsilyloxy)butyl]-$N^1,N^4,N^9$, $N^{12}$-tetrakis(mesitylsulfonyl)-spermine (3): Sodium hydride (60%, 1.0 g, 25 mmol) was added in portions with stirring under $N_2$ at 0° C. to a solution of 2 (9.31 g, 10.0 mmol) in DMF (20 mL). After stirring at room temperature for 30 min, t-butyl(4-iodobutoxy)dimethylsilane (7.86 g, 25 mmol) was added in one portion. The mixture was stirred overnight at room temperature and then partitioned between $H_2O$—$CH_2Cl_2$ (100 mL/100 mL). Organic phase was separated and the aqueous phase was extracted three times with $CH_2Cl_2$ (50 mL). Combined organic phases were washed with $NaHCO_3$ (1 M) solution and then dried on $MgSO_4$. After evaporation, pasty residue was purified by flash chromatography with 1:4 AcOEt:cyclohexane as eluant. The fractions containing 3 were evaporated to a pasty oil which was further washed with cold pentane to eliminate fast moving impurity and then pumped in vacuo to afford 9.97 g (76%) of 3 as an oil: TLC (AcOEt/cyclohexane 1:4): $R_f$=0.28. —IR (KRS-5): 2937, 1604, 1471, 1320, 1151, 1101, 838, 777, 657, 578 $cm^{-1}$ —$^1H$ NMR (300 MHz, $CDCl_3$): δ=−0.01 (s, 12H), 0.85 (s, 18H), 1.20-1.45 (m, 12H), 1.62 (m, 4H), 2.28 (s, 6H), 2.29 (s, 6H), 2.53 (s, 12H), 2.54 (s, 12H), 2.90-3.10 (m, 16H), 3.42 (t, J=6.1 Hz, 4H), 6.91 (s, 4H), 6.92 (s, 4H) —$^{13}C$ NMR (75 MHz, $CDCl_3$): δ=4.7, 18.9, 21.6, 23.4, 23.5, 24.1, 24.9, 25.7, 26.6, 30.4, 43.5, 43.6, 45.6, 45.7, 62.9, 132.59, 132.64, 133.8, 140.7, 143.0, 143.1 —MS-ESI (MeOH): m/z=1325.85 $[M+Na]^+$, 1303.83 $[M+H]^+$ —$C_{66}H_{110}N_4O_{10}S_4Si_2$ (Mw=1304.03) calcd. C, 60.79, H, 8.50, N, 4.30, 9.84; found C, 60.74, H, 8.55, N, 4.21, S, 9.63.

$N^1,N^{12}$-Bis(4-hydroxybutyl)spermine tetrahydrobromide (4): Hydrogen bromide in acetic acid (33% wt solution, 80 mL, 1.4 mol) was added dropwise to a solution of 3 (9.87 g, 7.57 mmol) and phenol (29.0 g, 0.31 mol, 40 equiv.) in $CH_2Cl_2$ (80 mL). The reaction mixture was stirred overnight at room temperature. On cooling with an ice bath, cold water (100 mL) was added with stirring. Organic layer was separated and extracted three times with water (20 mL). Combined aqueous layers were washed five times with $CH_2Cl_2$ (30 mL) and evaporated to dryness. Resulting humid solid residue was suspended in ether, triturated with spatula and the supernatant ether layer was discarded. These operations were repeated (five times) until a solid suspension was obtained. After evaporation and drying in vacuo, compound 4 was obtained as a solid (5.32 g). This crude materiel was used without further purification: $^1H$ NMR (300 MHz, $D_2O$): δ=1.75-2.10 (m, 12H), 2.27 (m, 4H), 3.15-3.35 (m, 16H), 3.76 (t, J=12.2 Hz, 4H). —$^{13}C$ NMR (75 MHz, $D_2O$): δ=22.9, 23.2, 23.4, 29.0, 45.0, 45.2, 47.7, 48.3, 61.5. —MS-ESI (MeOH): m/z=347.39 $[M+H]^+$.

$N^1,N^{12}$-Bis(4-(trifluoroacetoxy)butyl)-$N^1,N^4,N^9,N^{12}$-tetrakis(trifluoroacetyl)spermine (5) (from 4 with $TFA_2O$/$NEt_3$): To a suspension of 4 (5.3 g, 7.6 mmol) in $CH_2Cl_2$ (50 mL), triethylamine (11.5 g, 114 mmol, 15 equiv.) was added in one portion. The mixture was cooled on an ice-bath and trifluoroacetic anhydride (19.1 g, 90.9 mmol, 12 equiv.) was added dropwise with stirring under $N_2$. The mixture was stirred at room temperature for 3.5 h. After cooling on an ice-bath, the resulting solution was washed three times with cold water (20 mL), dried on MgSO$_4$ and then evaporated to afford an oily residue (11.7 g) which contains as secondary product of this reaction, (TFA)$_2$C=CH—NEt$_2$ (ref Schreber, S. L., *Tetrahedron Lett* 1980, 21, 1027). This was eliminated by two successive flash chromatography (eluant 1:1-60:40 AcOEt:cyclohexane and then 5-10% Et$_2$O/CH$_2$Cl$_2$) to afford 5 (5.59 g, 81%) as an oil: TLC (AcOEt/cyclohexane 1:1): R$_f$=0.25. —IR (KRS-5): 2955, 1789, 1690, 1467, 1352, 1197, 1147, 759, 731, 692 cm$^{-1}$. —$^1$H NMR (300 MHz, CDCl$_3$): δ=1.52-2.06 (m, 16H), 3.33-3.49 (m, 16H), 3.38 (m, 4H). —$^{13}$C NMR (75 MHz, CDCl$_3$): This spectrum is complicated by rotational isomerism of four amide groups. Only high intensity resonance signals are described as following: δ=23.3, 23.9, 24.1, 24.8, 25.3, 25.6, 26.0, 26.55, 26.61, 44.4, 44.8, 45.7, 46.1, 46.4, 47.3, 48.0, 56.6, 67.3, 67.5, 116.6 (q, J=288 Hz), 156.9, 157.4, 157.8, 158.6.

N$^1$,N$^{12}$-Bis(4-hydroxybutyl)-N$^1$,N$^4$,N$^9$N$^{12}$-tetrakis(trifluoroacetyl)spermine (6): To a solution of 5 (5.39 g, 5.84 mmol) in MeOH (50 mL), NaHCO$_3$ (0.1 g, solid) was added in one portion and the resulting suspension was stirred for 2 h at room temperature. After evaporation, oil residue was dissolved in CH$_2$Cl$_2$ (affording a suspension of some fibrous NaHCO$_3$) and purified by flash chromatography eluting with 5-10% MeOH/CH$_2$Cl$_2$ to afford 3.61 g (85%) of 6 as an oil: TLC (MeOH 5%/CH$_2$Cl$_2$): R$_f$=0.14. (MeOH 10%/CH$_2$Cl$_2$): R$_f$=0.45. —$^1$H NMR (300 MHz, CDCl$_3$): δ=1.51-2.02 (m, 18H), 3.33-3.51 (m, 16H), 3.68 (m, 4H). —MS-ESI (MeOH): m/z=753.33 [M+Na]$^+$. —C$_{26}$H$_{38}$F$_{12}$O$_6$.H$_2$O (Mw—748.60) calcd. C, 41.72, H, 5.39, N, 7.48, F, 30.45; found C, 41.97, H, 5.26, N, 7.37, F, 30.14.

Preparation of 6 from 4 (with TFA$_2$O/pyridine, then NaHCO$_3$): To a suspension of 4 (15.3 g, 22.8 mmol) in CH$_2$Cl$_2$ (100 mL) and pyridine (44 mL, 0.54 mol), trifluoroacetic anhydride (46 mL, 0.33 mol) was added dropwise with cooling on an ice bath and with stirring under N$_2$. The mixture was stirred at room temperature for 3 h. The excess of trifluoroacetic anhydride was decomposed by addition of cold water (100 mL) with cooling on an ice bath, then the resulting solution was extracted with CH$_2$Cl$_2$ (four times 100 mL+50 mL+25 mL×2). The combined extracts were washed with cold water (50 mL×3), dried on MgSO$_4$ and then evaporated to afford crude 5 (19.4 g, 92%) as oil. This oil was dissolved in MeOH (100 mL). NaHCO$_3$ (solid, 0.1 g) was added and the suspension was stirred overnight. After evaporation of solvent, the residue was purified by flash chromatography with 5-7% MeOH:CH$_2$Cl$_2$ as eluant to afford 10.1 g (61%) of 6 as an oil.

N$^1$-[4-(Dimethoxytrityloxy)butyl]-N$^{12}$-(4-hydroxybutyl)-N$^1$,N$^4$,N$^9$,N$^{12}$-tetrakis(trifluoro-acetyl)spermine (7): To a solution of 6 (1.46 g, 2.00 mmol) in pyridine (3 mL), DMTCI (757 mg, 2.23 mmol) was added using 1 mL of pyridine to rinse. The reaction mixture was stirred for 4 h at room temperature under N$_2$ and then pyridine was repeatedly removed by coevaporation with toluene. Residue was purified by two successive flash chromatography (eluant 2-5% MeOH/CH$_2$Cl$_2$ and then 10-15% acetone/CH$_2$Cl$_2$) to afford 7 (879 mg, 43%) as foam and bis-DMT derivative 8 (648 mg, 24%). Starting diol 6 was also recovered (350 mg, 24%). Data of 7: TLC (acetone/CH$_2$Cl$_2$ 1:9): R$_f$=0.20. —$^1$H NMR (300 MHz, CDCl$_3$): δ=1.51-2.03 (m, 17H), 3.11 (m, 2H), 3.32-3.51 (m, 16H), 3.71 (m, 2H), 3.81 (s, 6H), 6.84 (m, 4H), 7.19-7.46 (m, 9H) —MS-ESI (MeOH): m/z=1055.52 [M+Na]$^+$ —C$_{47}$H$_{56}$F$_{12}$N$_4$O$_8$ (Mw=1032.95) calcd. C, 54.65, H, 5.46, N, 5.42, F, 22.07; found C, 54.46, H, 5.58, N, 5.37, F, 21.63.

Compound (7) from diol (6) and bis-DMT derivative (8): To a solution of 6 (1.4 g, 1.9 mmol) and 8 (2.5 g, 1.9 mmol) in CH$_2$Cl$_2$, trifluoroacetic acid (50 μL, 0.6 mmol) was added and stirred at room temperature for 30 min. The solution was washed three times with Na$_2$CO$_3$ 1 M solution, dried on MgSO$_4$ and evaporated. Residue was separated by flash chromatography (column diameter: 50 mm, SiO$_2$ height: 15 cm) using successively 5% AcOEt/CH$_2$Cl$_2$ (750 mL), 33% AcOEt/CH$_2$Cl$_2$ (500 mL), 7% MeOH/CH$_2$Cl$_2$ (500 mL) and 10% MeOH/CH$_2$Cl$_2$ (500 mL) to afford 8 (1.1 g), 7 (1.2 g) and 6 (1.3 g).

Spermine tethered phosphoramidite (1): To a solution of 7 (844 mg, 817 μmol) and triethylamine (230 μL, 1.65 mmol, 2 equiv.) in CH$_2$Cl$_2$ (4 mL), 2-cyanoethyl-(N,N-diisopropylamino)chlorophosphite (205 μL, 0.92 mmol, 1.1 equiv.) was added and the mixture was stirred under N$_2$ at room temperature for 40 min. The reaction mixture was passed through SiO$_2$ column (diameter: 20 mm, height: 15 cm) saturated with NEt$_3$ (NEt$_3$ 1% in CH$_2$Cl$_2$:cyclohexane 1:2; 400 mL) using NEt$_3$ 1% in CH$_2$Cl$_2$:cyclohexane 1:2 (125 mL) and then NEt$_3$ 1% in CH$_2$Cl$_2$:cyclohexane 1:1 100 mL to give 1 (735 mg, 73%) as an oil: $^1$H NMR (200 MHz, CDCl$_3$): δ=1.13-1.35 (m, 12H), 1.51-2.06 (m, 16H), 2.66 (t, J=6.4 Hz, 2H), 3.11 (m, 2H), 3.32-3.98 (m, 20H), 3.81 (s, 6H), 6.84 (m, 4H), 7.15-7.51 (m, 9H). —$^{31}$P NMR (81 MHz, CDCl$_3$): 148.06, 148.13, 148.19, 148.3 (splitting due to amide rotational isomerism).

EXAMPLE 2: SYNTHESIS, PURIFICATION AND CHARACTERIZATION OF DECAMER OLIGONUCLEOTIDES HAYING FORMULA (WHEREIN CACCGTAGCG IS SEQ ID NO:3)

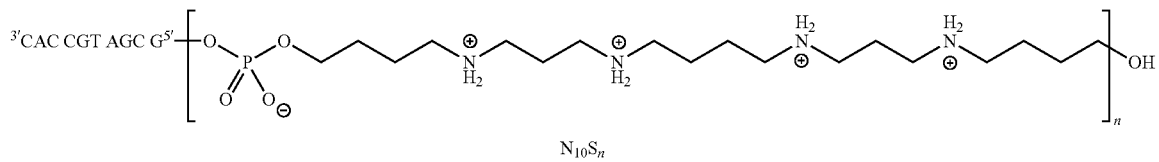

$N_{10}S_n$

Said oligonucleotides will be hereinafter designated by $N_{10}S_n$ (N10=an oligonucleotide moiety; S=a spermine residue and n=1-6).

Automated Synthesis:

A series of decamer oligonucleotides of identical sequences N10=3'CACCGTAGCG5' (SEQ ID NO:8) appended with increasing numbers of spermine residues S was synthesized using standard solid-phase cyanoethyl phosphoramidite chemistry on a Expedite DNA synthesizer, according to the following scheme:

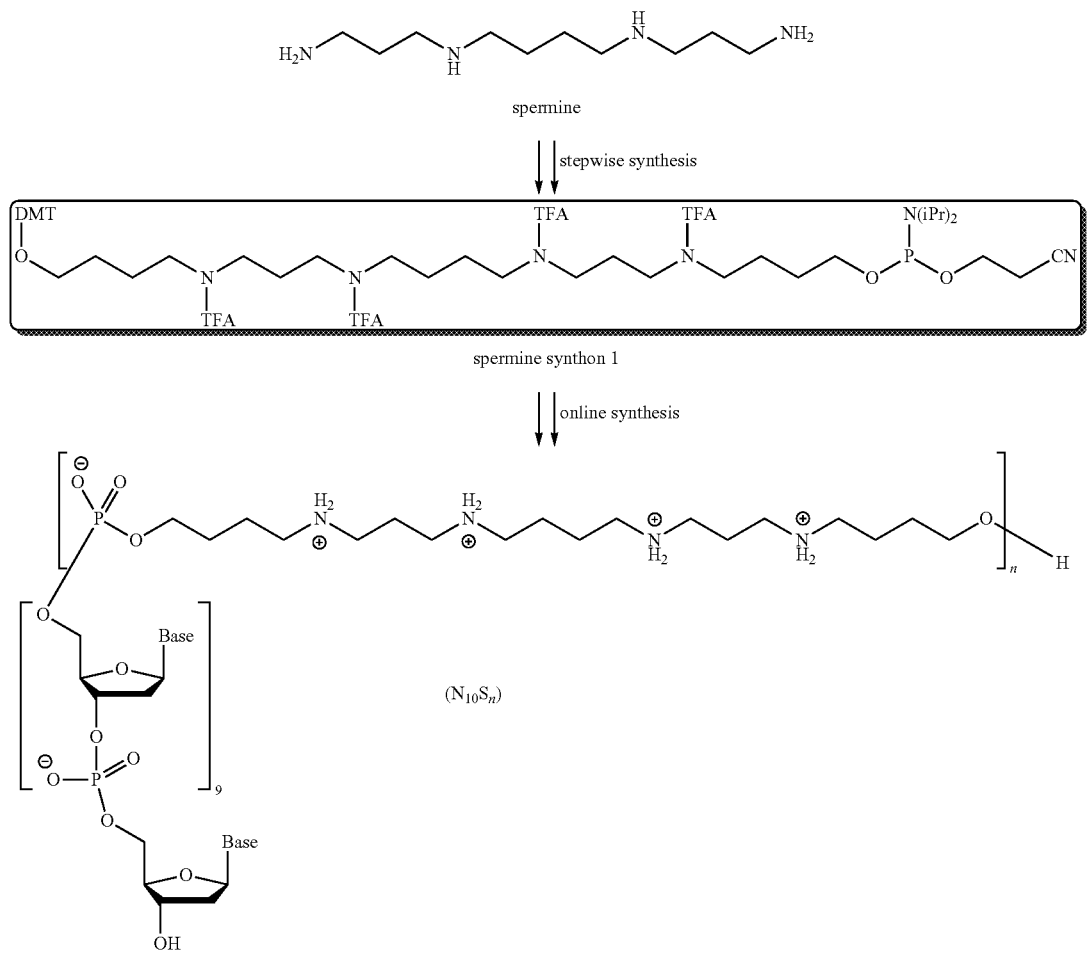

the last N moiety being a nucleoside according to the classical oligonucleotide synthesis.

Reagents used for automated DNA synthesis were purchased from Glen Research (Eurogentec).

During the automated synthesis, the standard 1 µmol coupling cycle was used, except for coupling of the spermine phosphoramidite 1 which was done with prolonged coupling time (15 min) and using a slightly more concentrated phosphoramidite solution (90 mg amidite in 1 mL acetonitrile). Trityl fractions were collected, diluted and analyzed in a spectrophotometer to determine the stepwise coupling yields.

The coupling yields of the four natural nucleotides exceeded 97%, while the yields of the spermine phosphoramidite coupling were between 90 and 96% in the above coupling conditions.

In all cases, the DMT-ON (ON=oligonucleotide) mode was used, keeping the 5'-end DMT group uncleaved on oligomers for purification-identification purposes.

Post-Synthetic Treatment:

After automated synthesis, cleavage from the solid support and complete deprotection of oligomers were done using standard conditions (treatment with concentrated aqueous ammonia for 90 min at room temperature for cleavage and then overnight at 55° C. for deprotection).

Purification:

The first two anionic oligonucleotides $N_{10}S_1$ and $N_{10}S_2$ were initially purified in DMT-on state by standard HPLC procedure on a reverse-phase nucleosil C-18 column (Macherey-Nagel 10×250 mm) with a linear gradient of acetonitrile (5-35% in 20 min) in 20 mM ammonium acetate solution (pH 7). Purified oligonucleotides were then detritylated by treatment with $AcOH/H_2O=4/1$ (500 mL) at r.t. for 20 min. After dilution with water (5 mL), DMT-OH was eliminated by ether extraction (3×2 mL) and the aqueous phase was concentrated to afford the oligomers.

The HPLC analysis of oligonucleotides $N_{10}S_1$ and $N_{10}S_2$ is given in FIG. 1 a reverse-phase nucleosil C-18 column (Macherey-Nagel 4.6×250 mm) with a linear gradient of acetonitrile (5-35% in 20 min) in 20 mM ammonium acetate solution (pH 7): a) $N_{10}S_1$, crude, DMT-ON; b) $N_{10}S_1$ purified c) $N_{10}S_2$, crude, DMT-ON; d) $N_{10}S_2$, purified. *Benzamide; **Truncated sequences.

The neutral oligomer $N_{10}S_3$ and the cationic oligomers $N_{10}S_4$, $N_{10}S_5$ and $N_{10}S_6$ (with or without DMT group) were purified using Poly-PakII™ (Glen Research/Eurogentec) columns according to the instruction given by manufacturer except for the final oligonucleotide elution which was done with acetonitrile/concentrated aqueous ammonia/water (20:4:80). The fractions containing the oligonucleotide could be revealed using a TLC plate. After gathering the fractions, solvents were removed by lyophilization. The oligomers thus obtained were generally contaminated by benzamide. It was eliminated by extraction with ether (three times) after dissolution in diluted aqueous ammonia solution (50 mM). The purified oligonucleotides were dissolved in diluted aqueous ammonia solution (50 mM), and their concentration was determined using the following extinction coefficient (260 nm, mol$^{-1}$dm$^3$cm$^{-1}$):

$$\epsilon=(15.4N_A+11.5N_G+7.4N_c+8.7N_T)\times 0.9\times 10^3.$$

The HPLC analysis of purified oligonucleotides is given in FIG. 2: anion exchange column (Dionex PA-100 9×250 mm) with a linear gradient of NaCl (100-350 mM over 10 min)/NaOH 25 mM (pH 12.4): a) $N_{10}S_1$, b) $N_{10}S_2$, c) $N_{10}S_3$, d) $N_{10}S_4$, e) $N_{10}S_5$, f) $N_{10}S_6$.

Due to the conjugation chemistry employed, each polyamine comes with a phosphate group, hence contributing for a net additional cationic charges. Seven oligonucleotides, $(NH_{10}S_n)3^{n-9}$ n=0 . . . 6, with overall charges −9, −6, −3, 0, +3, +6, +9 when fully ionized, where thus available in amounts ranging from 80 to 250 nanomoles.

Figure 3:
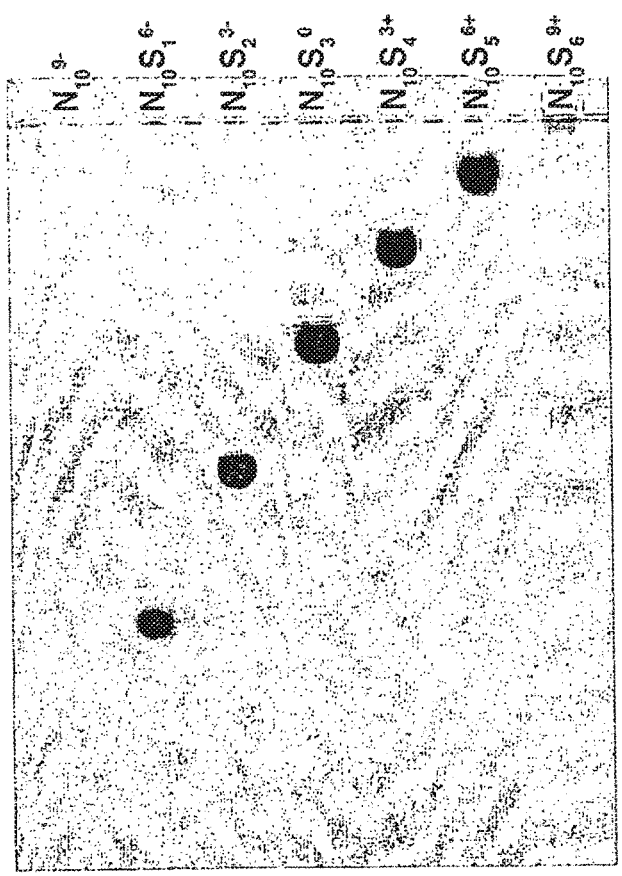

Electrophoretic Mobility:

Their migration in an electric field at pH7 was studied by polyacrylamide gel electrophoresis and revealed by silver mirror staining. Compounds (0.5 nmol) in 10 µL loading buffer (10 mM HEPES pH 7.4, 150 mM NaCl, glycerol) were loaded onto a nondenaturating polyacrylamide gel (15% in TAE pH 7). Electrophoresis was run at 5 V/cm for 17 h at 4° C. Silver staining was performed according to Rabilloud et al, Electrophoresis, 1987, 9, 288-291. The results are given in FIG. 3. Oligonucleotide $N_{10}$ (lane 1) without spermine was moving fast towards the anode and showed only faint silver staining in conditions where polyamine-containing oligonucleotides were revealed.

Spontaneous Exchange of $N_{10}$ with $N_{10}C_{10}$

Figure 4:
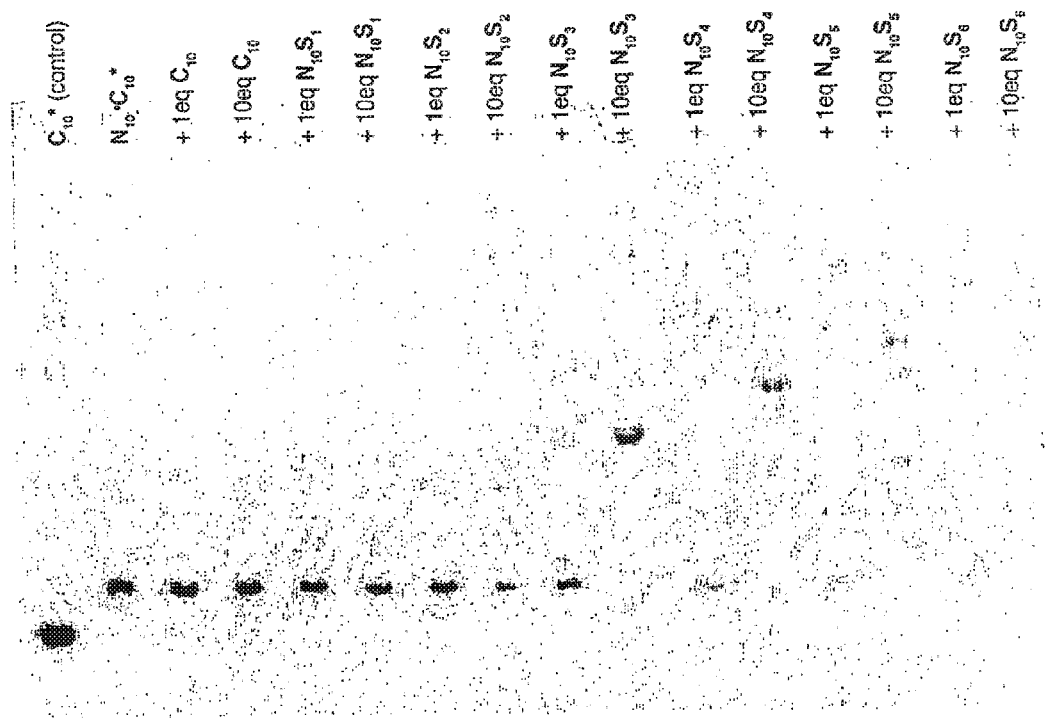

Oligonucleotide $C_{10}$ (where C is the nucleotide complementary to N) (50 pmol 15 or 500 pmol) was added to the fluorescent $N_{10}.C_{10}$* duplex solution (50 pmol in HEPES 10 mM pH 7.4, NaCl 150 mM). The mixtures were incubated 4 h at 37° C., 20° C. or 10° C. and loaded onto a nondenaturing polyacrylamide gel (15% in TAE pH 7). Electrophoresis was performed at 4° C. for 17 h at 5 V/cm. $C_{10}$* fluorescence was detected by scanning the gel using a Typhoon 8600 Imager. As shown by the results given in FIG. 4, the spontaneous exchange of $N_{10}$ with $N_{10}C_{10}$ is not significant at 10° C.

Strand Exchange Between $N_{10}$ and $N_{10}S_n$

The strand replacement capacity of $N_{10}S_n$ towards the natural duplex $N_{10}C_{10}$ was tested in physiological salt conditions.

Spermine conjugates $N_{10}S_n$ (50 or 500 pmol) were added to a fluorescent $N_{10}C_{10}$* duplex solution (50 pmol in 10 mM HEPES pH 7.4, 150 mM NaCl). The mixtures were incubated 4 h at 10° C. and loaded onto a nondenaturing polyacryamide gel (15% in TAE pH 7). Electrophoresis was performed at 4° C. for 17 h at 5 V/cm. Fluorescence was detected by scanning the gel using a Typhoon 8600 Imager.

Figure 5:
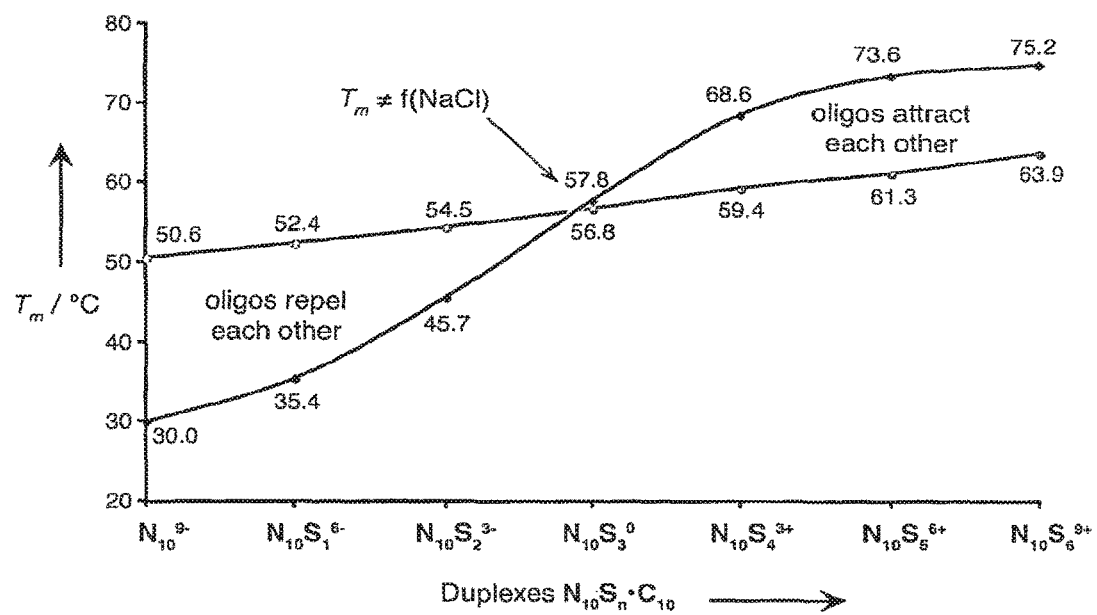
Figure 6:
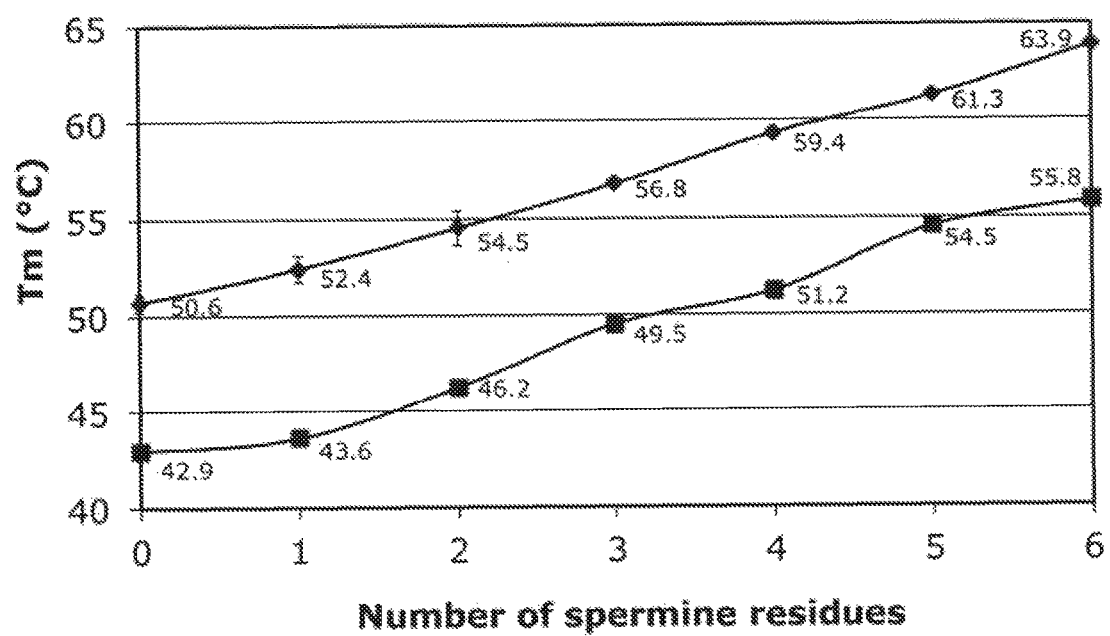
Figure 7A:
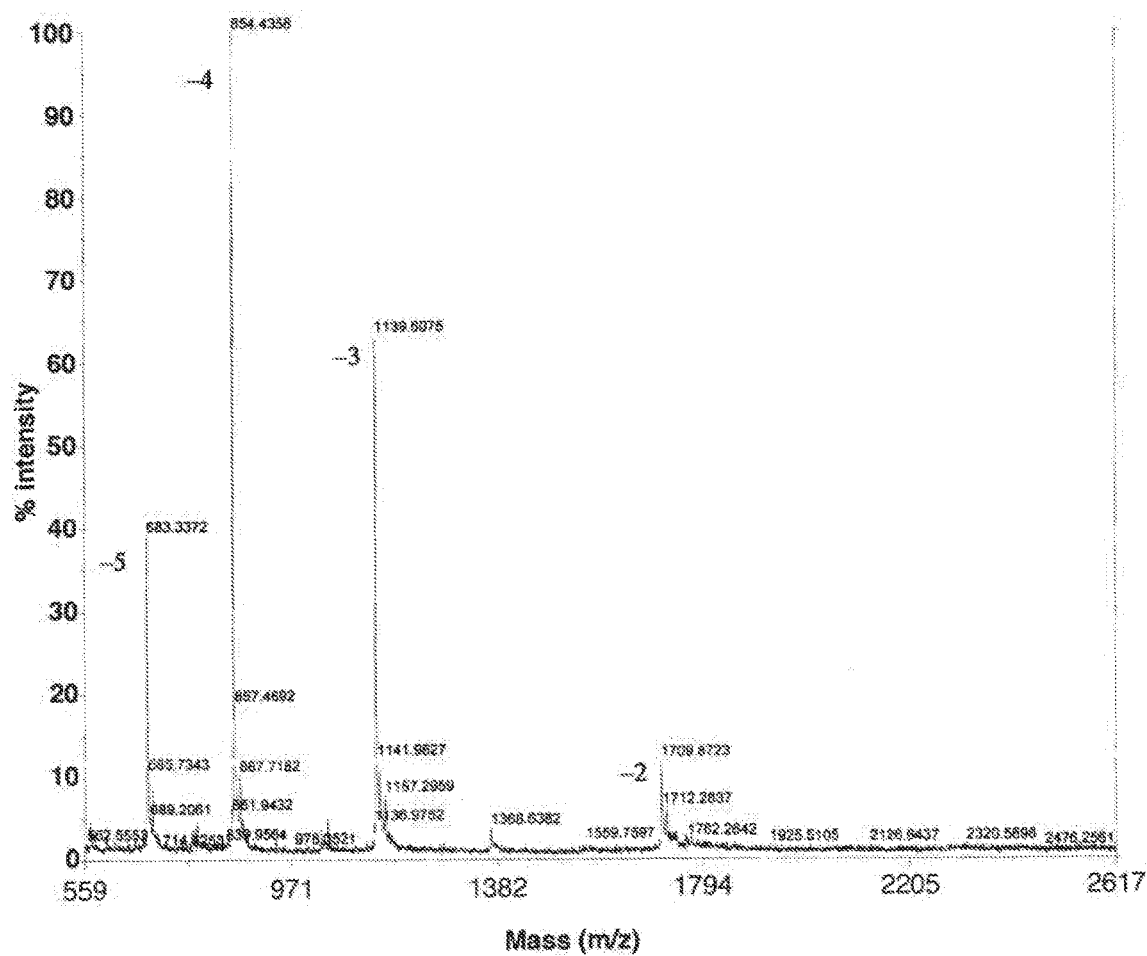
FIG. 7A: comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2); ESI-MS of N10S1; m/z calcd. 3419.84, found 3419.80.
Figure 7B:
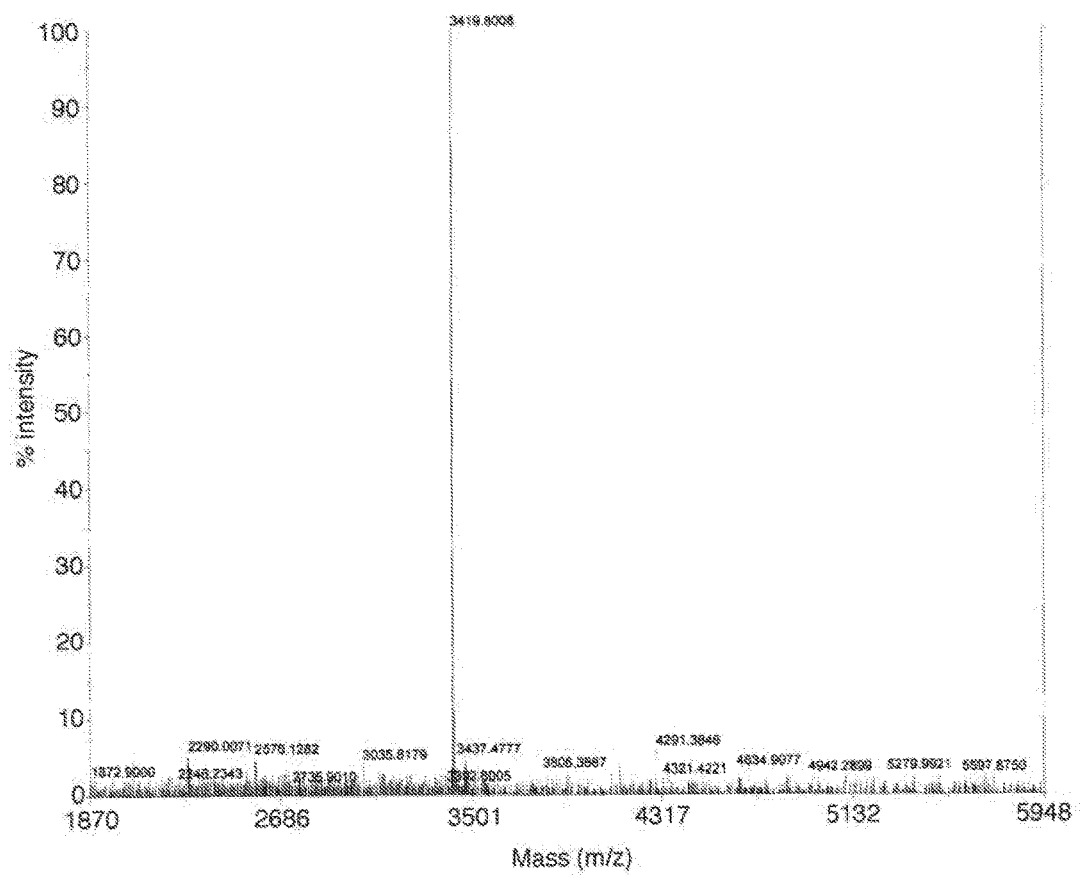
FIG. 7B.
Figure 7C:
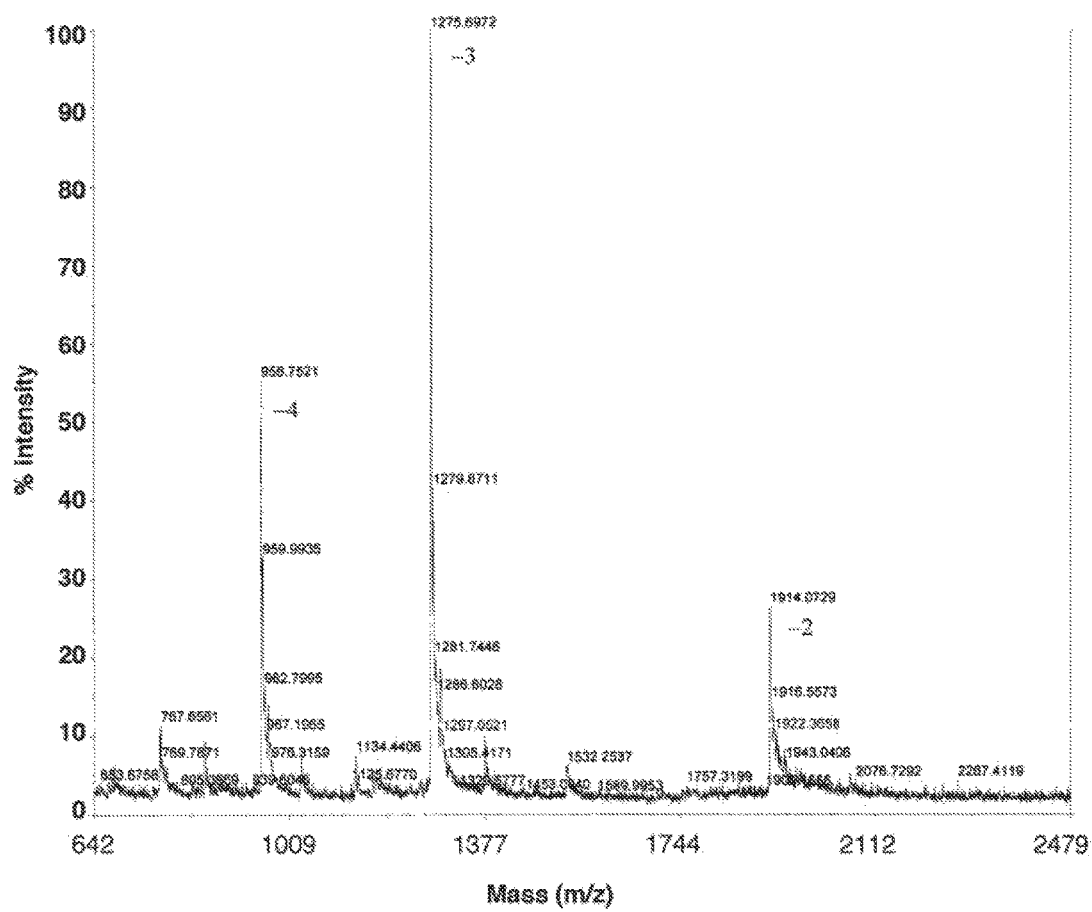
FIG. 7C: ESI-MS of N10S2; m/z calcd. 3828.12, found 3829.12—comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2)
Figure 7D:
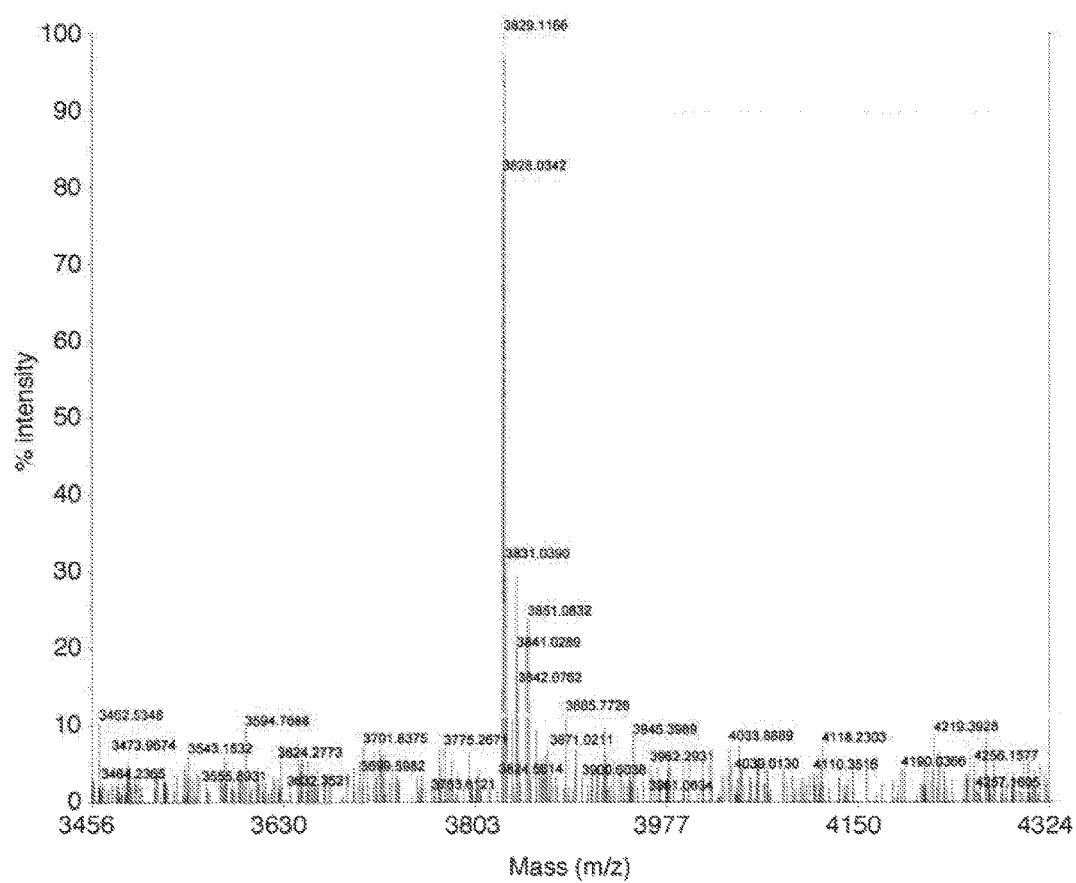
FIG. 7D.
Figure 7E:
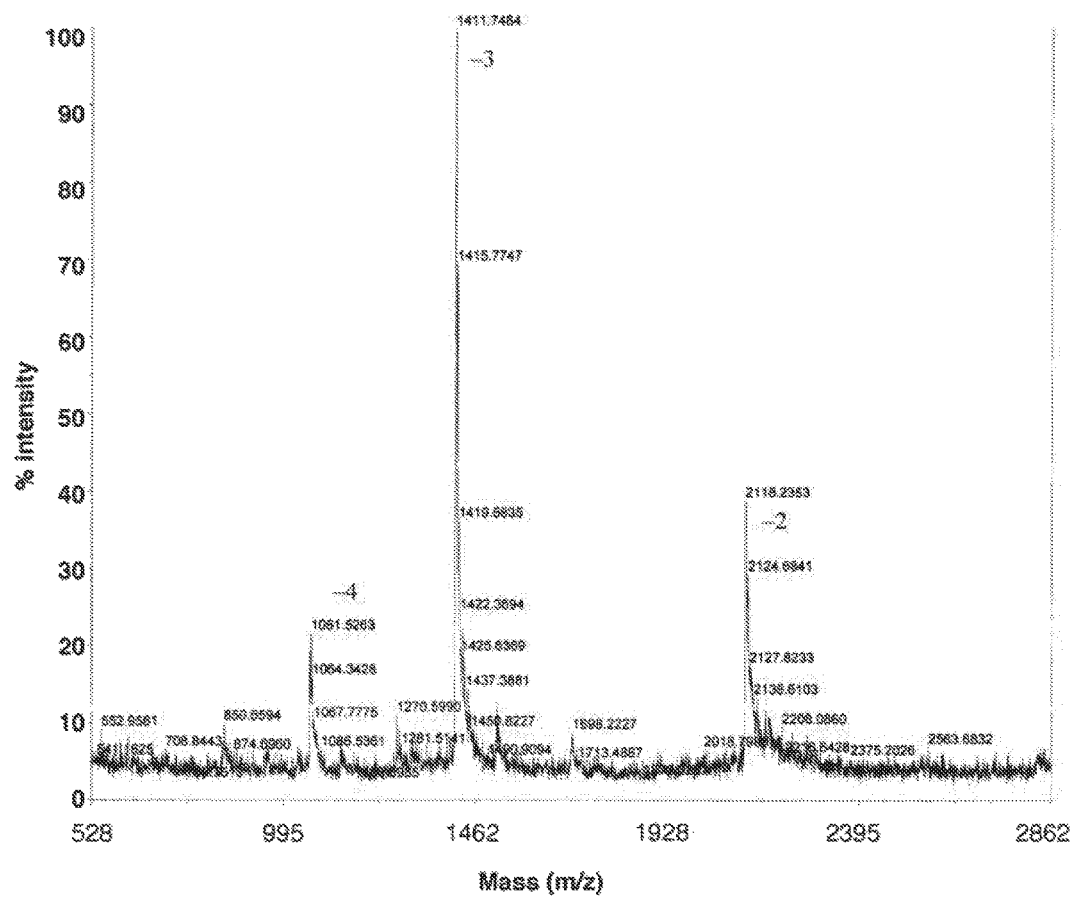
FIG. 7E: ESI-MS of N10S3; m/z calcd. 4236.44, found 4238.40—comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2)
Figure 7F:
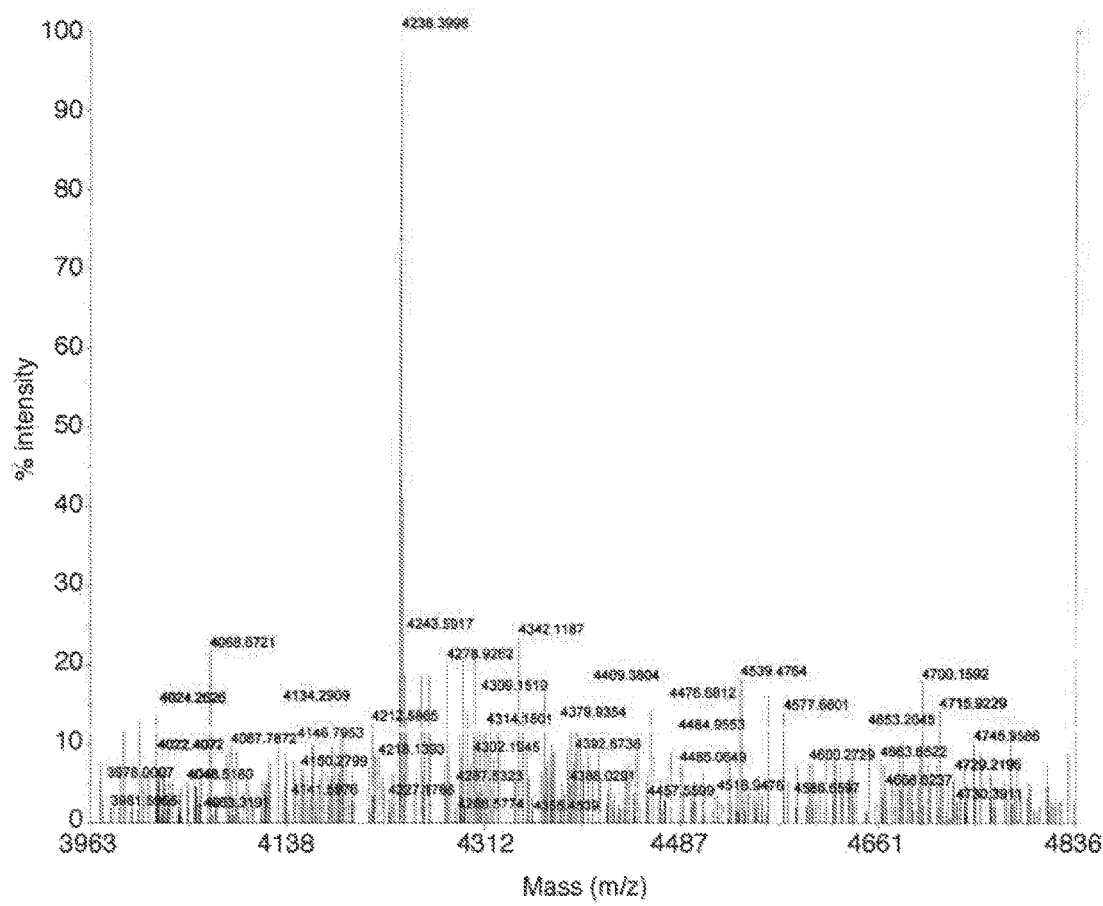
FIG. 7F.
Figure 7G:
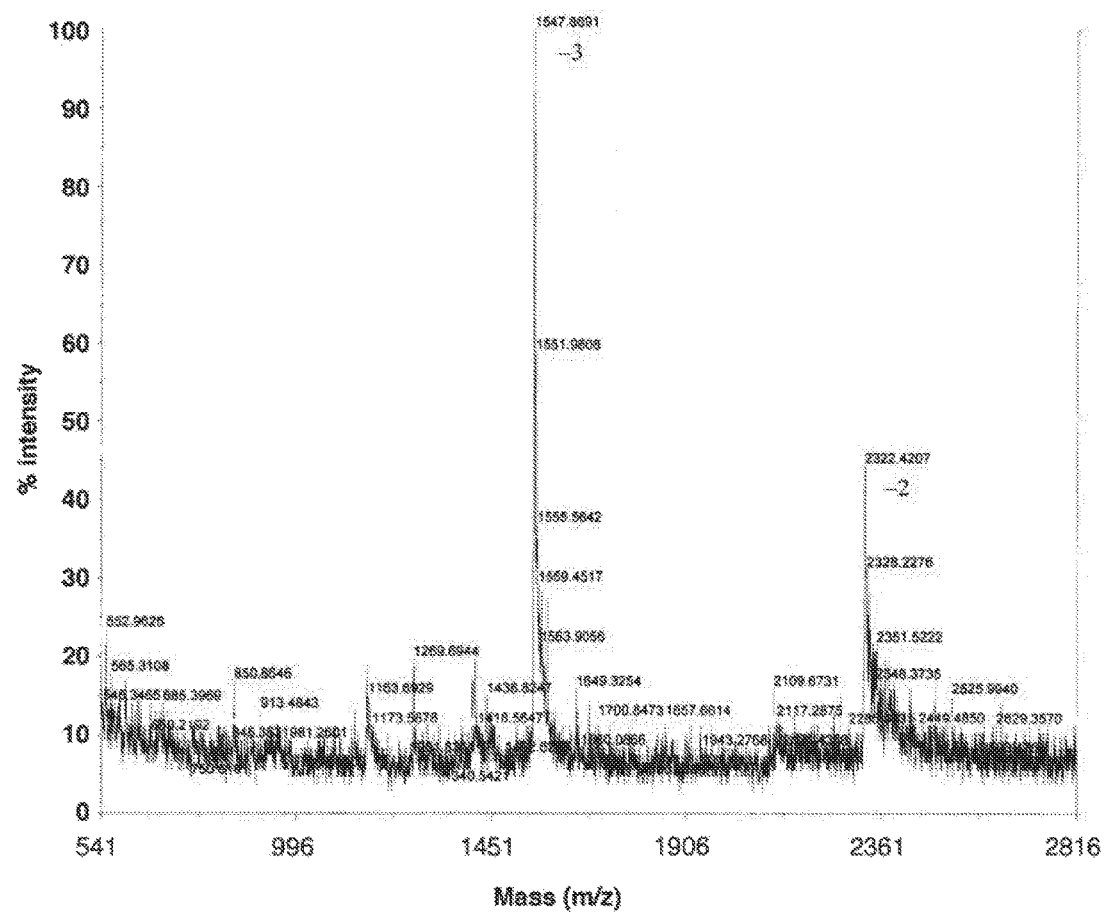
FIG. 7G: ESI-MS of N10S4; m/z calcd. 4644.69, found 4644.23—comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2)
Figure 7H:
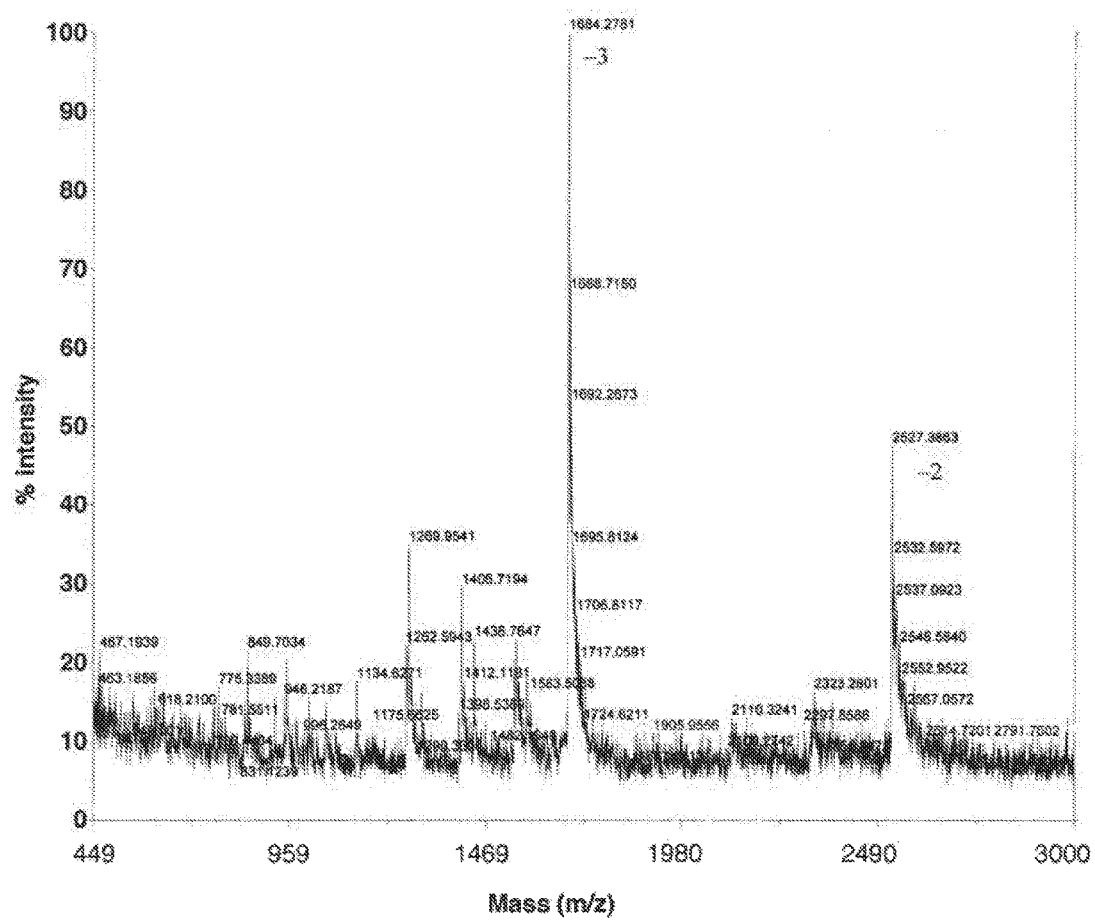
FIG. 7H: ESI-MS of N10S5; m/z calcd. 5052.98, found 5053.80—comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2)
Figure 7I:
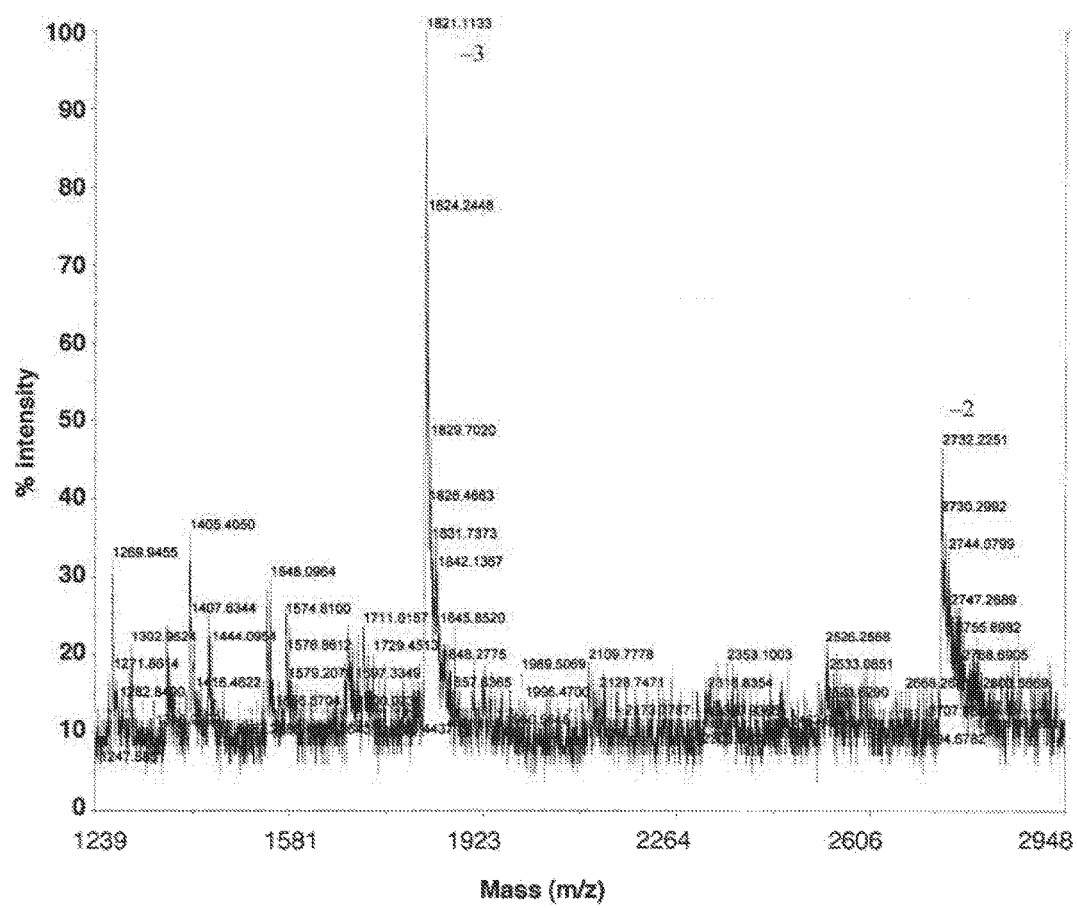
FIG. 7I: ESI-MS of N10S6; m/z calcd. 5464.08, found 5463.90—comparative results of melting temperatures of duplexes formed by $N_{10}S_n$ (n=0-6) with 5'GTGGCATCGC3' (SEQ ID NO:1) and with 5'GTGGCGTCGC3' (SEQ ID NO:2), FIG. 8, ES-MS analysis of purified $N_{10}S_n$ (n=1-6) oligonucleotides, FIG. 9A, HPLC trace of phosphorothioate oligonucleotide $N_{12}S_{11}F$, FIG. 9B, HPLC trace of phosphorothioate oligonucleotide $N_{12}S_2F$, FIG. 10A, MALDI-TOF MS spectra of $N_{12}S_2F$, FIG. 10B, MALDI-TOF MS spectra of $N_{12}S_{11}F$, FIG. 11A, HPLC trace of $N_{20}S_5F$, FIG. 11B, HPLC trace of $N_{14}S_4F$, FIG. 12A, MALDI-TOF MS spectra of $N_{14}S_4F$, FIG. 12B, MALDI-TOF MS spectra of $N_{20}S_5F$, FIG. 13A, strand invasion of pGL2 and pGL3 plasmids by $N_{14}S_nF$.

Spermine conjugation had a profound effect on the strand exchange reaction as shown in FIG. 5. The band corresponding to $N_{10}C_{10}$ became weaker as the number of spermine residues of the competing $N_{10}S_n$ increased, in favour of a slower-moving, less anionic $N_{10}S_nC_{10}$ complex. This effect was especially pronounced for $N_{10}S_3$, i.e., for conjugates which no longer bear a formal negative charge. Indeed, spermine is clipping duplex DNA structures by forming an interstrand network of $NH_2^+$ bidentate hydrogen bonds in the minor groove, hence will favour $N_{10}S_n$ binding over $N_{10}$. Yet an additional favourable kinetic factor may operate when strand exchange occurs in a preformed $(N_{10}S_n)^{3n-9}/(N_{10}C_{10})^{18}$ electrostatic complex, which can be the case for n>3.

Melting Temperatures of $N_{10}S_nC_{10}$ Duplexes

Stabilities of double stranded nucleic acids were compared by measuring their melting temperature, i.e., the temperature where complementary strands cooperatively fall apart. Optical density (O.D.) was thereof recorded at 260 nm of solutions of $N_{10}S_nC_{10}$ vs. temperature T.

Melting temperatures $T_m$ were measured in HEPES 10 mM pH 7.4 (black line, rhombi) and in HEPES 10 mM pH 7.4+150 mM NaCl (grey line, circles). Melting profiles of all duplexes (3.75 nmol in 1 ml buffer) were obtained using a CARY 4000 Spectrophotometer equipped with a temperature control unit by gradually heating the samples (1° C./min) while recording their absorbance at 260 nm. Duplex melting results in a hyperchromic shift and $T_m$ is the temperature where the first derivative curve dO.D./dT=f(T) reaches its maximum. The results are given in FIG. 5.

The natural duplex melted at $T_m$=30° C. in 10 mM HEPES pH 7.4 (FIG. 5). Conjugation of increasing numbers of spermines led to remarkable $T_m$ increases. $N_{10}S_6.C_{10}$ melted at $T_m$=75.2° C., some 45° C. higher than the natural duplex. The $T_m$=f(n) curve showed a sigmoidal shape with an inflection for the neutral $N_{10}S_3$ oligonucleotide.

Melting temperatures were also recorded in physiological salt conditions. The Tm=f(n) curve appeared much damped and, remarkably, crossed the previous curve for $N_{10}S_3$. Thus for n<3, both $N_{10}S_n$ and $C_{10}$ oligonucleotides are anionic and repel each other in the duplex; increasing the solution salt concentration shields repulsive forces hence increases $T_m$. For n>3 $N_{10}S_n$ becomes cationic and attracts $C_{10}$; here salt-induced electrostatic shielding decreases stability.

For the neutral $N_{10}S_3$ duplex stability is independent of salt concentration.

Comparison of Melting Temperatures of Duplexes Formed by $N_{10}S_n$ (n=0-6) with 5'GTGGCATCGC3' (SEQ ID NO:1) and with 5'GTGGCGTCGC3' (SEQ ID NO:2)

A single base pair mismatch discrimination of the oligonucleotide-spermine conjugates was tested. Within the sequence context of $C_{10}$=5'GTGGCATCGC3' (SEQ ID NO:1), literature data recommended a centrally-located A-to-G conversion as being the most stringent test.

Melting temperatures $T_m$ were measured in HEPES 10 mM pH 7.4+NaC 150 mM. Melting profiles of all duplexes (3.75 nmol in 1 mL buffer) were obtained using a CARY 4000 Spectrophotometer equipped with a temperature control unit by gradually heating the samples (1° C./min) while recording their absorbance at 260 nm. $T_m$ is the temperature where the first derivative curve dO.D./dT=f(T) reaches its maximum. The results are given on FIG. 7 (rhombi correspond to 5'GTGGCATCGC3' (SEQ ID NO:1) and triangles to 5'GTGGCGTCGC3' (SEQ ID NO:2)).

The transition temperature of the natural $N_{10}.C_{10}$ duplex in 150 mM NaCl fell from 50.6° C. to 42.9° C., i.e., DTm=7.7° C. when the mismatch was present. In principle, stability increase due to nonspecific, end-conjugated electrostatic forces should not impair base pair specificity, which is expressed as ΔΔG. This is indeed what was observed, as the complementary and mismatch target oligonucleotide showed quasi-parallel $T_m$=f(n) curves with average $\Delta T_m$=7.9° C.

ES-MS Analysis of Purified $N_{10}S_n$ Oligonucleotides.

Figure 8:
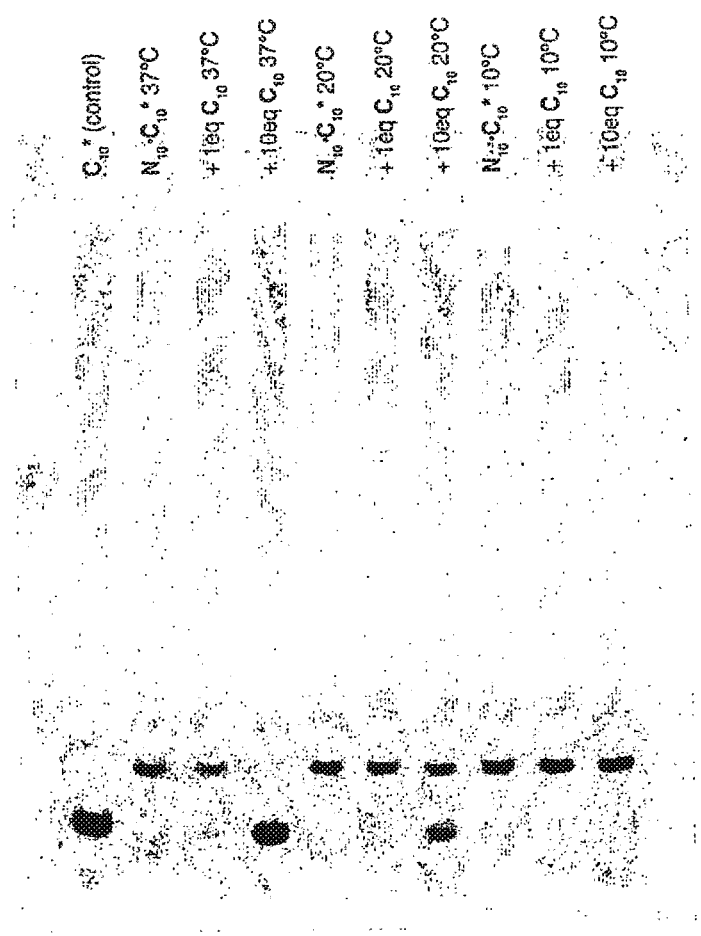

Oligonucleotides were dissolved in 50% aqueous acetonitrile (v/v) containing 1% triethylamine at a final concentration of 5×10$^{-5}$ M. 100 mL aliquots were introduced into the ion source of an Applied Biosystems Mariner 5155 mass spectrometer at a flow rate of 5 mL/min. The results are given in FIG. 8 (insets: deconvoluted spectra): a) $N_{10}S_1$, b) $N_{10}S_2$, c) $N_{10}S_3$, d) $N_{10}S_4$, e) $N_{10}S_5$, f) $N_{10}S_6$. Ionization of the neutral and cationic oligomers $N_{10}S_{3-6}$ became more difficult and it was necessary to accumulate several spectra to obtain acceptable signal-to noise ratio.

EXAMPLE 3: SYNTHESIS, PURIFICATION AND CHARACTERIZATION OF 12-MER THIOPHOSPHATE OLIGONUCLEOTIDES HAVING FORMULA (WHEREIN GCGACTCATGAA IS SEQ ID NO:4)

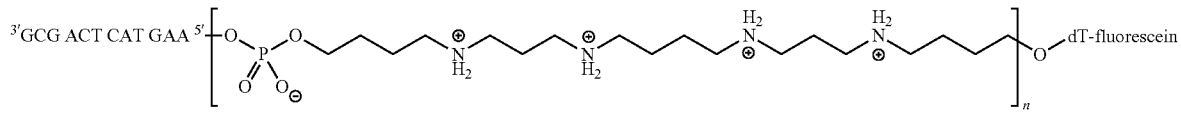

Oligonucleotide thiophosphate $N_{12}S_nF$

Said oligonucleotides will be thereafter designated by $N_{12}S_nF$ (N=a 12-mer oligonucleotide thiophosphate moiety; S=a spermine residue and n=2 or 11; F=fluorescein conjugated to thymine).

Automated Synthesis:

Twelve-mer thiophosphate oligonucleotides of sequence $N_{12}=^{3'}$GCGACTCATGAA$^{5'}$ (SEQ ID NO:4) appended with two or 11 spermine residues S were synthesized using solid-phase cyanoethyl phosphoramidite chemistry on an Expedite DNA synthesizer. Ultramild CE phosphoramidites and ultramild supports (Glen Research/Eurogentec) were used in order to avoid oligomer cleavage during work-up. A standard sulfurizing reagent (Glen Research/Eurogentec) was used to generate the phosphorothioate linkages in the 12-mer oligonucleotide moiety. Fluorescein-dT phosphoramidite (Glen Research/Eurogentec) was used for 5'-end labelling. Spermine phosphoramidite coupling was performed using the coupling protocol described in example 2.

Trityl fractions were collected, diluted and analyzed in a spectrophotometer to determine the stepwise coupling yields.

In all cases, the DMT-ON mode was used, keeping the 5'-end DMT group uncleaved on oligomers for purification-identification purposes.

Post-Synthetic Treatment:

After automated synthesis, cleavage from the solid support and complete deprotection of oligomers were performed by treatment with concentrated aqueous ammonia overnight at room temperature.

Purification:

DMT-ON compounds $N_{12}S_2F$ and $N_{12}S_{11}F$ were purified using Poly-Pak II™ columns (Glen Research/Eurogentec) according to instructions given by the manufacturer.

Figure 9A:
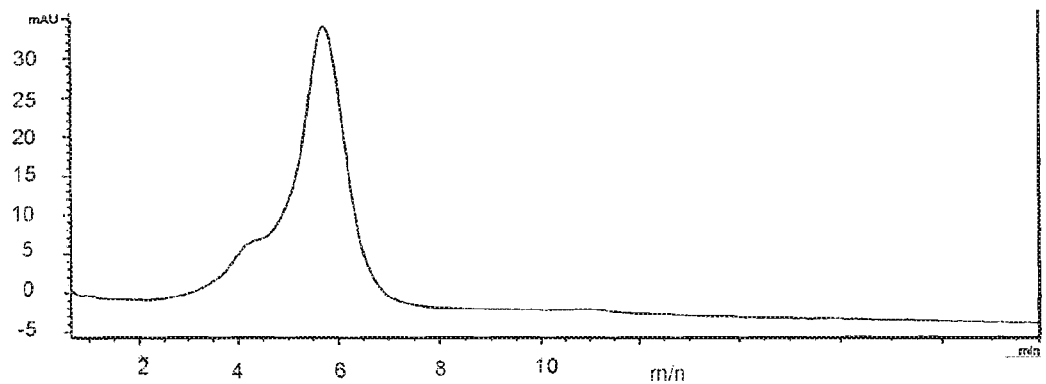
Figure 9B:
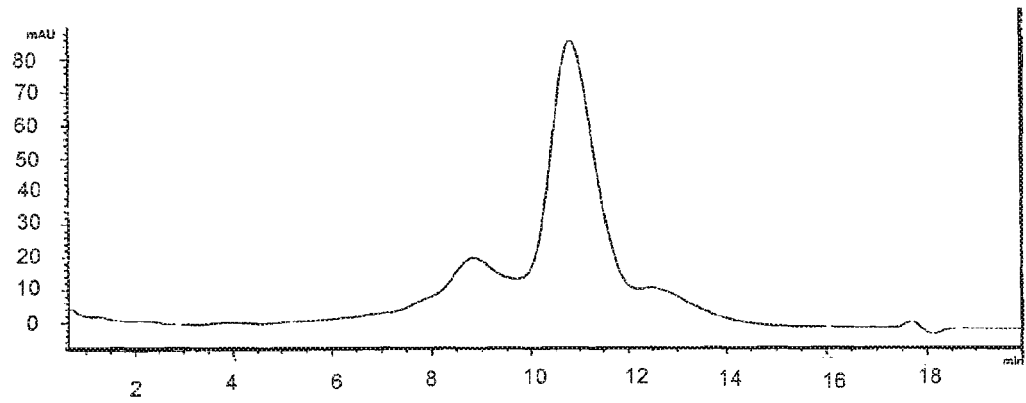

Purified oligonucleotides $N_{12}S_nF$ (n=2, 11) were analyzed on an anion exchange column (SAX1000-8) in aqueous basic conditions (100 mM ammonia, pH 11) using a NaCl gradient (0.75-2.5 M in 20 min). HPLC traces are shown in FIG. 9 (A: $N_{12}S_{11}F$, B: $N_{12}S_2F$).

MALDI-TOF MS Analysis of Purified Oligonucleotides.

Figure 10A:
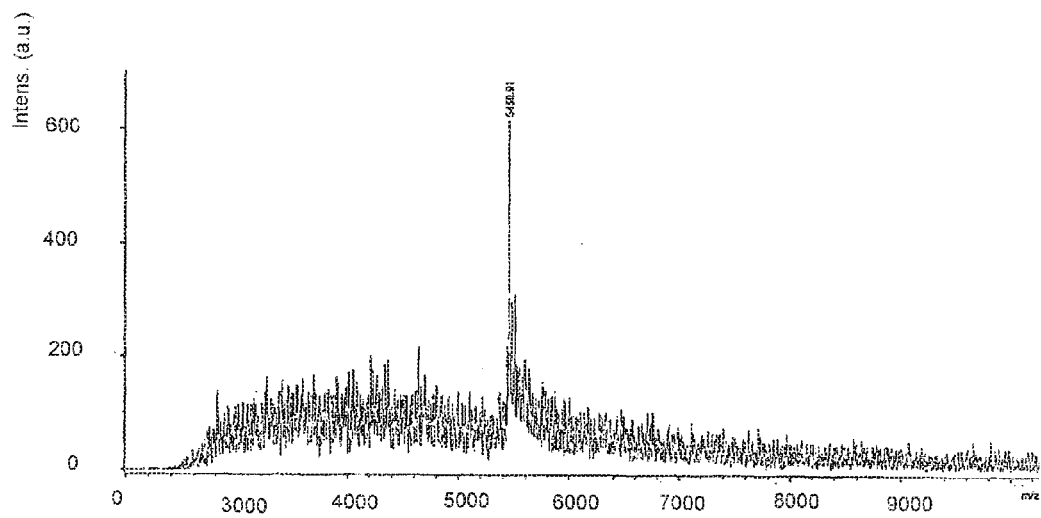
Figure 10B:
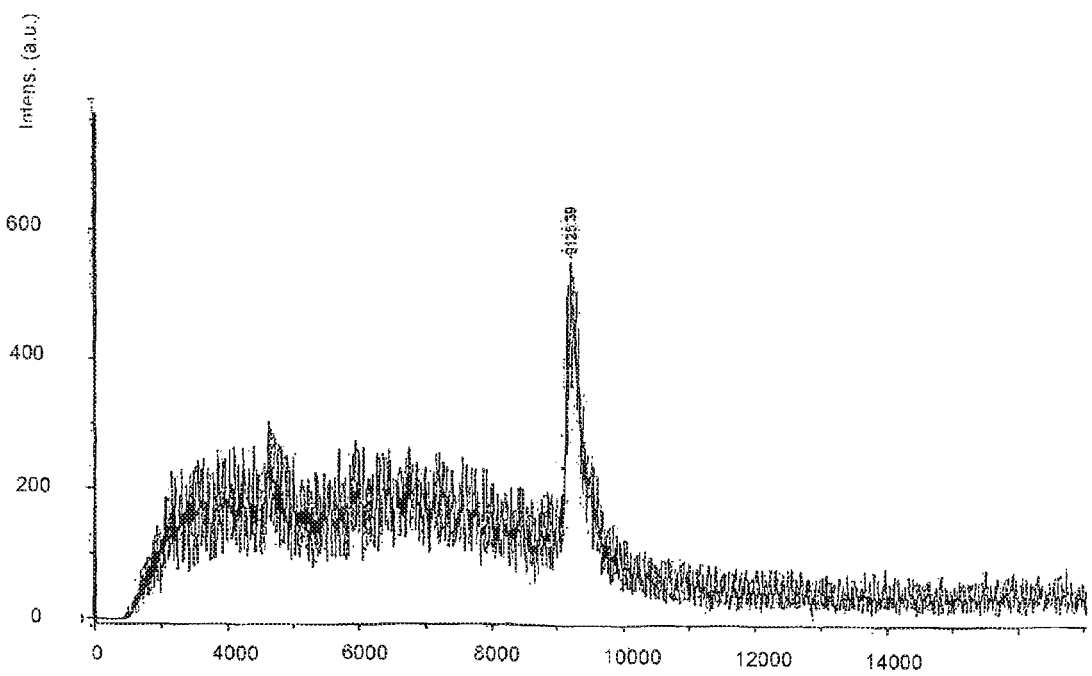

Oligonucleotides were dissolved in 500 μL of deionized water. The sample and HPA matrix were mixed together on the plate. Once crystallized, the sample was analyzed with a BRUKER Ultraflex MS apparatus. Results are given in FIG. 10A: $N_{12}S_{11}F$ calc 5460, found 5459 (upper) and FIG. 10B: $N_{12}S_{11}F$ calc: 9135 found: 9125 (lower).

EXAMPLE 4: PLASMID DNA STRAND INVASION WITH 14-MER AND 20-MER FLUORESCENT OLIGONUCLEOTIDES (WHEREIN TCGCCAAGGTAGAA IS SEQ ID NO:5)

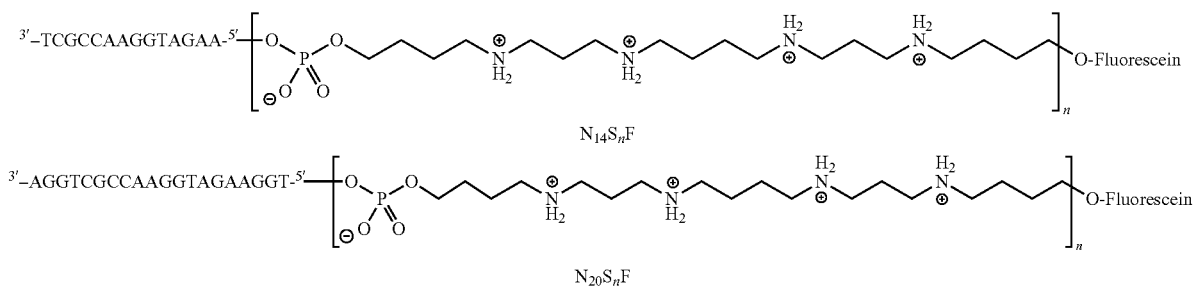

$N_{14}S_nF$ $N_{20}S_nF$

Compounds shown above will be thereafter designated by $N_{14}S_nF$ (N=an oligonucleotide moiety; S=a spermine residue with n=24; F=a fluorescein residue) and by $N_{20}S,F$ (N=an oligonucleotide moiety; S=a spermine residue with n=3-5; F=a fluorescein residue).

Figure 12A:
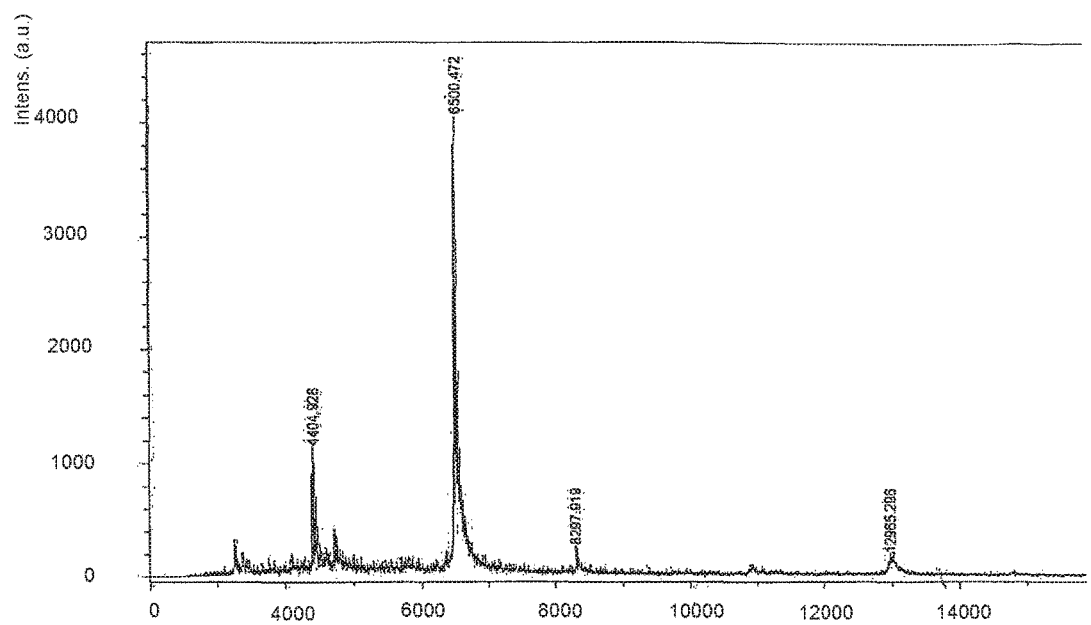
Figure 12B:
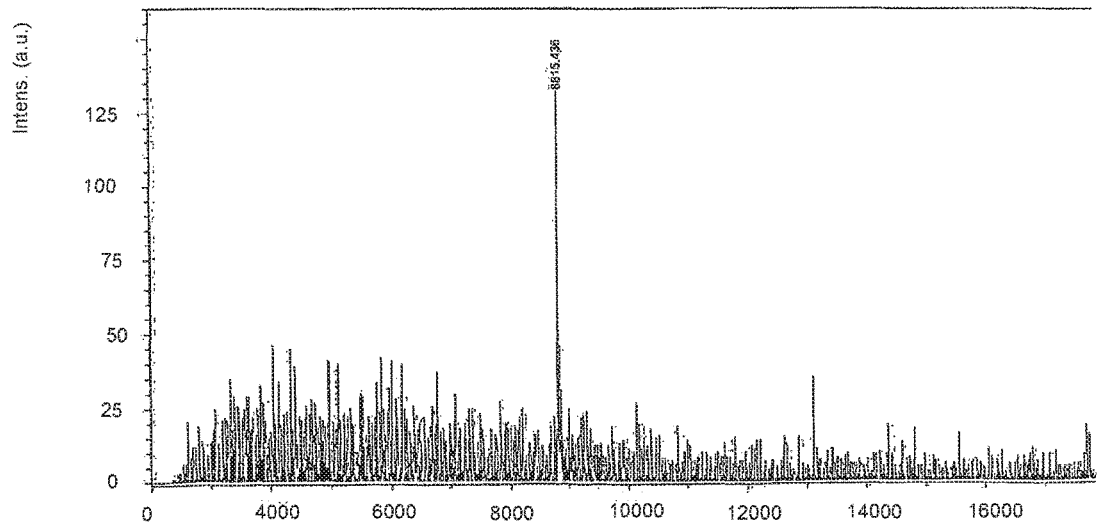

These fluorescent oligonucleotides were synthesized following the procedure described in example 2. 5'-Fluorescein phosphoramidite (Glen Research/Eurogentec) was used for 5'-end labelling. Analytical HPLC traces and MALDI-TOF MS spectra for the most substituted $N_{14}S_4F$ and $N_{20}S_5F$ compounds are shown in FIGS. 11 and 12 as proofs of purity and structure ($N_{14}S_4F$ calc 6470, found 6478; $N_{20}S_5F$ calc 8813, found 8815), respectively.

Oligonucleotide sequences of $N_{14}S_nF$ and $N_{20}S_nF$ were chosen within the Luciferase gene sequence of the pGL3 control plasmid (Promega). To assess the sequence specificity of strand invasion, pGL2 control plasmid (Promega) was used. The GL2 Luciferase sequence is 95% identical to GL3, and the sequences targeted by $N_{14}S_nF$ and $N_{20}S_nF$ contain respectively one and two mismatches.

The ability of $N_{14}S_nF$ and $N_{20}S_nF$ to strand-invade pGL3 and not pGL2 plasmids was tested in physiological salt and temperature conditions.

Fluorescent conjugates $N_{14}S_nF$ and $N_{20}S_nF$ (8.65 pmol) were added to a solution of plasmid (1.5 μg, 0.43 pmol in 10 mM HEPES pH 7.4, 150 mM NaCl). The mixtures were incubated 24 h at 37° C. and loaded onto an agarose gel (1.3% in TAE pH 7.4). Electrophoresis was performed at room temperature for 45 min after what fluorescein green emission was detected by scanning the gel using a Typhoon 8600 Imager. A red fluorescence picture of the gel was taken on an UV transilluminator following a 15 min incubation in ethidium bromide solution. The results are given in FIG. 13.

Red and green fluorescences are evidence of double stranded plasmid DNA and fluorescent oligonucleotide, respectively. Their colocalization with pGL3 and not with pGL2 is thus evidence for strand invasion. Compounds $N_{14}S_3F$ and $N_{20}S_nF$ showed a faint green fluorescent band associated with the plasmid when incubated with pGL3 and not with pGL2.

EXAMPLE 5: PENETRATION OF CATIONIC OLIGONUCLEOTIDES INTO CELLS

Figure 14A:
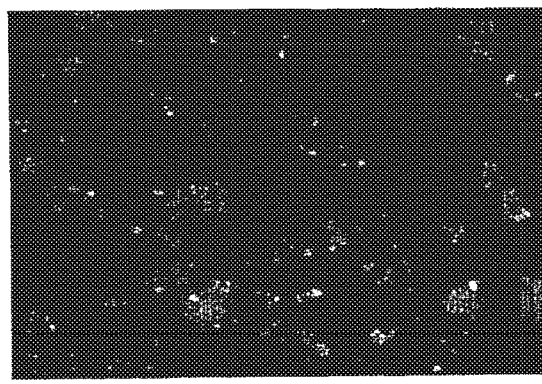
FIG. 14A penetration of the cationic oligonucleotide $F—S_{18}N_{19}$ into HeLa cells.
Figure 14B:
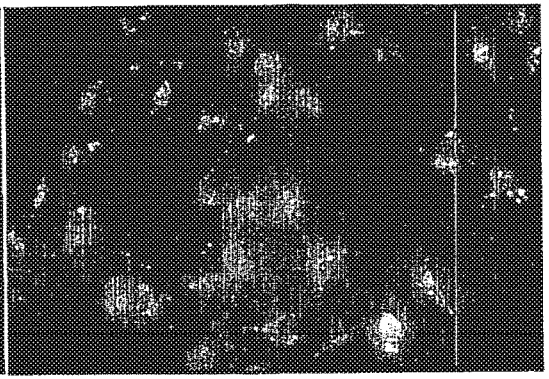
FIG. 14B penetration of the cationic oligonucleotide $F—S_{18}N_{19}$ into HeLa cells.

Hela cells, grown in 10% (v/v) fetal calf serum containing MEM medium, were plated at $50\text{-}60\times10^3$ cells/well into 4-well chambered borosilicate Lab-Tek dishes one day prior to the experiment. Complete medium was replaced by 0.5 ml serum-free MEM medium. A 5'-cationic fluorescein-conjugated oligonucleotide $F\text{—}S_{18}N_{19}$ (where $N_{19}$ is TCGAAGTACTCAGCGTAAG (SEQ ID NO:7)) formulation was prepared in sterile PBS. It was added to the cells to a final concentration of 2 μM. Four hours later, the medium was replaced by 1 ml of fresh serum-containing medium. A first picture was taken with a Zeiss axiovert 25 fluorescence microscope, equipped with a FITC filter (FIG. 14A, left). All cells became fluorescent, with some fluorescence located in intracellular vacuoles and, most importantly, also spread throughout the cytoplasm and nucleus. After 24 h, the medium was replaced with 1 ml of phenol red-free MEM medium. Propidium iodide (1 mM in water) was added to a final concentration of 10 μM. Ten minutes later, a second picture was taken showing a majority of propidiumless healthy cells that were still fluorescent (FIG. 14B, right). The control cells that were incubated in similar conditions with F—N19 oligonucleotide showed no fluorescence.

The invention thus provides a versatile automatic synthesis of cationic oligonucleotides that form fast and stable complexes with their complementary sequence even in a strand invasion context. Due to end conjugation, sequence selectivity remains as high as for natural oligonucleotides. Moreover, thanks to their cationic nature, intracellular delivery does not require complex formation with cationic carrier molecules. Taken together, these properties make oligonucleotide-oligocation conjugates attractive alternatives to oligonucleotides for molecular biology, diagnostics as well as therapeutic applications.

---

We claim:

1. A phosphoramidite reagent comprising the formula: $P(OR^9)(N(R^{10})_2)$—O—$R^1$—(X—$R2_n$)n1-X—$R^3$—O-Prot, where $R^1$, $R^2R^3$ and n1$R^1$, $R^2$ and $R^3$, identical or different are lower alkylene, n varies from 1 to 5, n1=2 to 20, X is a protected NH or NC(NH$_2$)$_2$, $R^9$ is CH$_2$CH$_2$CN or lower alkyl, $R^{10}$ is lower alkyl, or —N(R$^{10}$)$_2$ is pyrrolidino, piperidino or morpholino group, and Prot is a protecting group of dimethoxytrityl (DMT) or monmethoxytrityl (MMT); or $P(OR^9)(N(R^{10})_2)$—O—$R^4$—CH($R^5X^1$)—$R^6$—O-Prot where $R^4$, $R^5$, $R^6$ are lower alkylene, $X^1$ is a protected putrescine, spermidine or spermine, $R^9$ is CH$_2$CH$_2$CN or lower alkyl, $R^{10}$ is a lower alkyl, or —N(R$^{10}$)$_2$ is pyrrolidino, piperidino or morpholino group; or $P(OR^9)(NR^{10})_2)$—O—$R^7$-(aa)$_{n2}$-$R^8$—O-Prot where $R^7$ is lower alkylene and $R^8$ is a lower alkylene, $R^9$ is CH$_2$CH$_2$CN or lower alkyl, $R^{10}$ is a lower alkyl, or —N(R$^{10}$)$_2$ is pyrrolidino, piperidino or morpholino group, n2=2 to 20, (aa)$_{n2}$ is a peptide containing natural amino acids with cationic side chains and Prot is a protecting group of dimethoxytrityl (DMT) or monomethoxytrityl (MMT).

2. A phosphoramidite reagent comprising the formula:

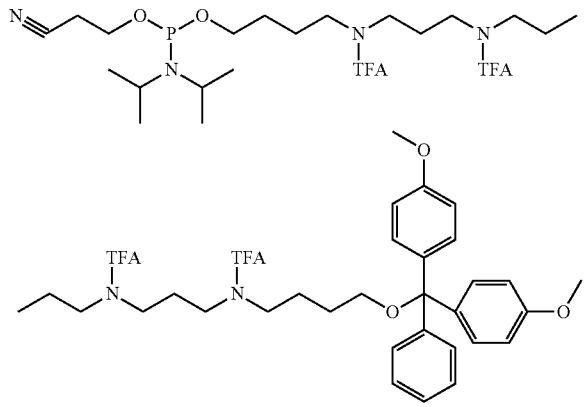

which is $N^1$-[4-(dimethoxytrityloxy)butyl]-$N^{12}$-[4-(phosphoramidite)butyl]-$N^1$,$N^4$,$N^9$,$N^{12}$-tetrakis(trifluoroacetyl) spermine.

3. A phosphoramidite reagent comprising is $N^1$-[4-(dimethoxytrityloxy)butyl]-$N^{12}$-[4-(phosphoramidite)butyl]-$N^1$,$N^4$,$N^9$,$N^{12}$-tetrakis(trifluoroacetyl) spermidine.

4. A phosphoramidite reagent comprising $N^1$-[4-(dimethoxytrityloxy)butyl]-$N^{12}$-[4-(phosphoramidite)butyl]-$N^1$,$N^4$,$N^9$,$N^{12}$-tetrakis(trifluoroacetyl) putrescine.

5. The phosphoramidite reagent according to claim 1, wherein $P(OR^9)(NR^{10})_2$—O—$R^7$-$(aa)_{n2}$-$R^8$—O-Prot where $R^7$ is lower alkylene and $R^8$ is a lower alkylene, $R^9$ is $CH_2CH_2CN$ or lower alkyl, $R^{10}$ is a lower alkyl, or —$N(R^{10})_2$ is pyrrolidino, piperidino or morpholino group, n2=2 to 20 and is $(aa)_{n2}$, which is a peptide containing protective cationic side chains of Arginine, Lysine, Ornithine, Histidine or Diaminopropionic acid and Prot is a protecting group of dimethoxytrityl (DMT) or monomethoxytrityl (MMT).

* * * * *

SEQUENCE LISTING

```
<160> NUMBER OF SEQ ID NOS: 8

<210> SEQ ID NO 1
<211> LENGTH: 10
<212> TYPE: DNA
<213> ORGANISM: Artificial sequence
<220> FEATURE:
<223> OTHER INFORMATION: Oligonucleotide

<400> SEQUENCE: 1
gtggcatcgc                                                            10

<210> SEQ ID NO 2
<211> LENGTH: 10
<212> TYPE: DNA
<213> ORGANISM: Artificial sequence
<220> FEATURE:
<223> OTHER INFORMATION: Oligonucleotide

<400> SEQUENCE: 2
gtggcgtcgc                                                            10

<210> SEQ ID NO 3
<211> LENGTH: 10
<212> TYPE: DNA
<213> ORGANISM: Artificial sequence
```

```
<220> FEATURE:
<223> OTHER INFORMATION: Oligonucleotide

<400> SEQUENCE: 3
caccgtagcg                                                              10

<210> SEQ ID NO 4
<211> LENGTH: 12
<212> TYPE: DNA
<213> ORGANISM: Artificial sequence
<220> FEATURE:
<223> OTHER INFORMATION: Oligonucleotide

<400> SEQUENCE: 4
gcgactcatg aa                                                           12

<210> SEQ ID NO 5
<211> LENGTH: 14
<212> TYPE: DNA
<213> ORGANISM: Artificial sequence
<220> FEATURE:
<223> OTHER INFORMATION: Oligonucleotide

<400> SEQUENCE: 5
tcgccaaggt agaa                                                         14

<210> SEQ ID NO 6
<211> LENGTH: 20
<212> TYPE: DNA
<213> ORGANISM: Artificial sequence
<220> FEATURE:
<223> OTHER INFORMATION: Oligonucleotide

<400> SEQUENCE: 6
aggtcgccaa ggtagaaggt                                                   20

<210> SEQ ID NO 7
<211> LENGTH: 19
<212> TYPE: DNA
<213> ORGANISM: Artificial sequence
<220> FEATURE:
<223> OTHER INFORMATION: Oligonucleotide

<400> SEQUENCE: 7
tcgaagtact cagcgtaag                                                    19

<210> SEQ ID NO 8
<211> LENGTH: 10
<212> TYPE: DNA
<213> ORGANISM: Artificial sequence
<220> FEATURE:
<223> OTHER INFORMATION: Oligonucleotide

<400> SEQUENCE: 8
gcgatgccac                                                              10
```